United States Patent
Egholm et al.

(10) Patent No.: US 6,451,588 B1
(45) Date of Patent: Sep. 17, 2002

(54) MULTIPARTITE HIGH-AFFINITY NUCLEIC ACID PROBES

(75) Inventors: Michael Egholm, Wayland, MA (US); Caifu Chen, Foster City, CA (US)

(73) Assignee: PE Corporation (NY), Foster City, CA (US)

( * ) Notice: Subject to any disclaimer, the term of this patent is extended or adjusted under 35 U.S.C. 154(b) by 19 days.

(21) Appl. No.: 09/610,155

(22) Filed: Jun. 30, 2000

(51) Int. Cl.[7] .............................. C12M 1/34; C12Q 1/68; C12P 19/34; C07H 21/02; C07H 21/04
(52) U.S. Cl. ..................... 435/287.2; 435/6; 435/91.1; 435/287.1; 536/23.1; 536/24.3; 536/24.33
(58) Field of Search ........................ 435/6, 91.1, 91.2, 435/183; 436/94; 536/23.1, 24.3, 24.33, 25.3

(56) References Cited

U.S. PATENT DOCUMENTS

| | | | | |
|---|---|---|---|---|
| 5,424,413 A | * | 6/1995 | Hogan et al. | 536/24.31 |
| 5,527,675 A | * | 6/1996 | Coull et al. | 435/6 |
| 5,639,609 A | | 6/1997 | Kruse-Mueller et al. | |
| 5,663,062 A | | 9/1997 | Sorge et al. | |
| 5,821,060 A | | 10/1998 | Arlinghaus et al. | |
| 5,854,410 A | | 12/1998 | Arnold, Jr. et al. | |
| 5,861,242 A | * | 1/1999 | Chee et al. | 435/5 |
| 5,935,791 A | | 8/1999 | Nadeau et al. | |
| 6,140,490 A | * | 10/2000 | Biesecker et al. | 536/24.31 |
| 6,255,476 B1 | * | 7/2001 | Vinayak et al. | 536/25.32 |

FOREIGN PATENT DOCUMENTS

| | | | |
|---|---|---|---|
| GB | 9801628.0 | * | 1/1998 |
| GB | WO 99/37806 | * | 7/1999 |
| WO | WO99/37806 | | 7/1999 |

OTHER PUBLICATIONS

Cardullo et al., Detection of nucleic acid hybridization by nonradiative fluorescence resonance energy transfer. Proc. Natl. Acad. Sci. USA, 85, 8790–8794, 1988.*

Pease et al., Light-generated oligonucleotide arrays for rapid DNA sequence analysis. Proc. Natl. Acad. USA 91, 5022–5026, May 1994.*

Laios et al., Novel hybridization assay configurations based on in vitro expression of DNA reporter molecules. Clin. Biochem. 31, 151–158, Apr. 1998.*

Kandimalla et al., "Design, Biochemical, Biophysical and Biological Properties of Cooperative Antisense Oligonucleotides," *Nucleic Acids Research* 23(*17*):3578–3584 (1995).

* cited by examiner

Primary Examiner—Ethan C. Whisenant
Assistant Examiner—Frank Lu
(74) Attorney, Agent, or Firm—Alex Andrus

(57) ABSTRACT

The invention provides a collection of probes useful for hybridizing to a target nucleic acid. The probes associate with each other, binding with high affinity to the target nucleic acid, to form three-way junctions and other complexes. At least one of the probes in each collection includes a nucleic acid analog. Methods using the probes in hybridization and as primers are also provided.

17 Claims, 15 Drawing Sheets

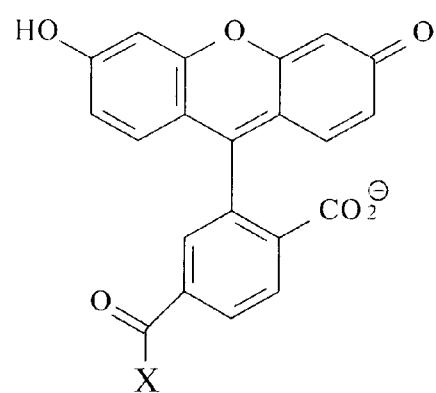
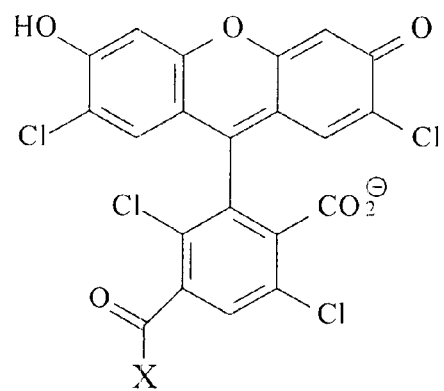
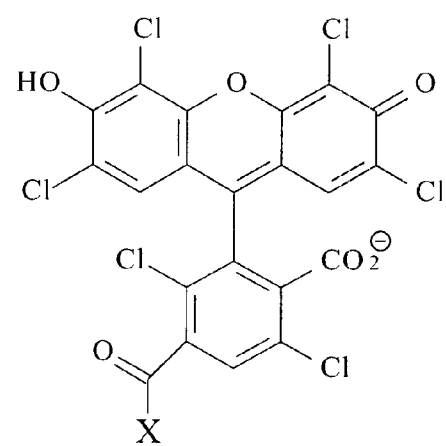
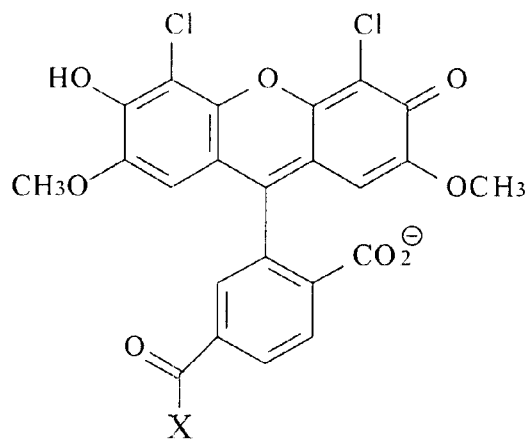
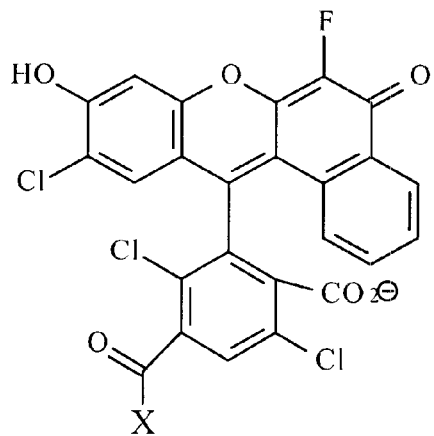
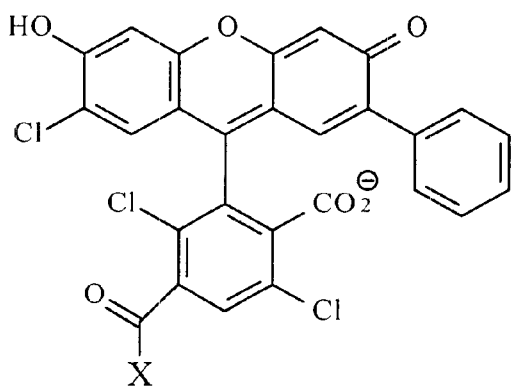
Figure 2A

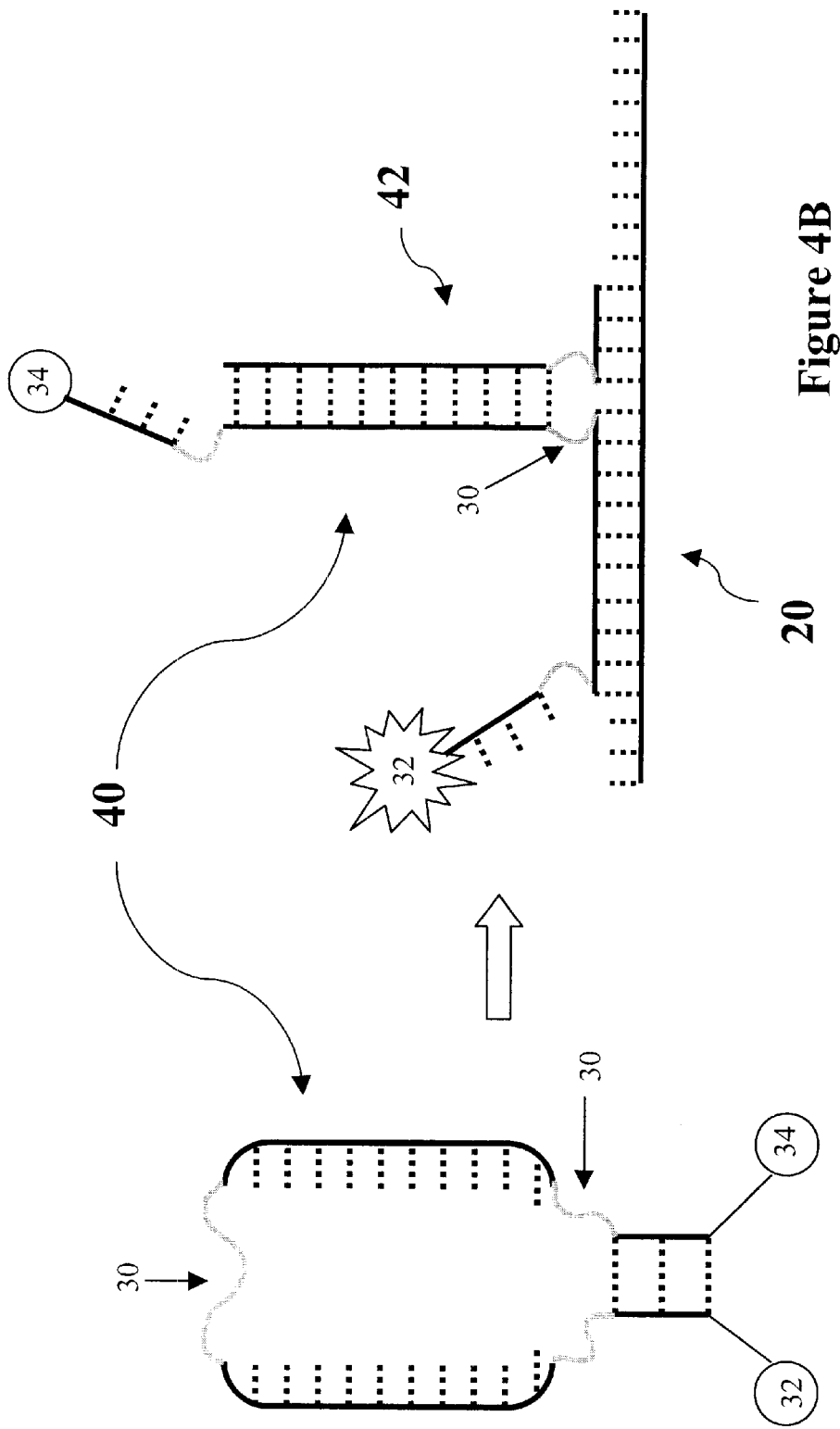

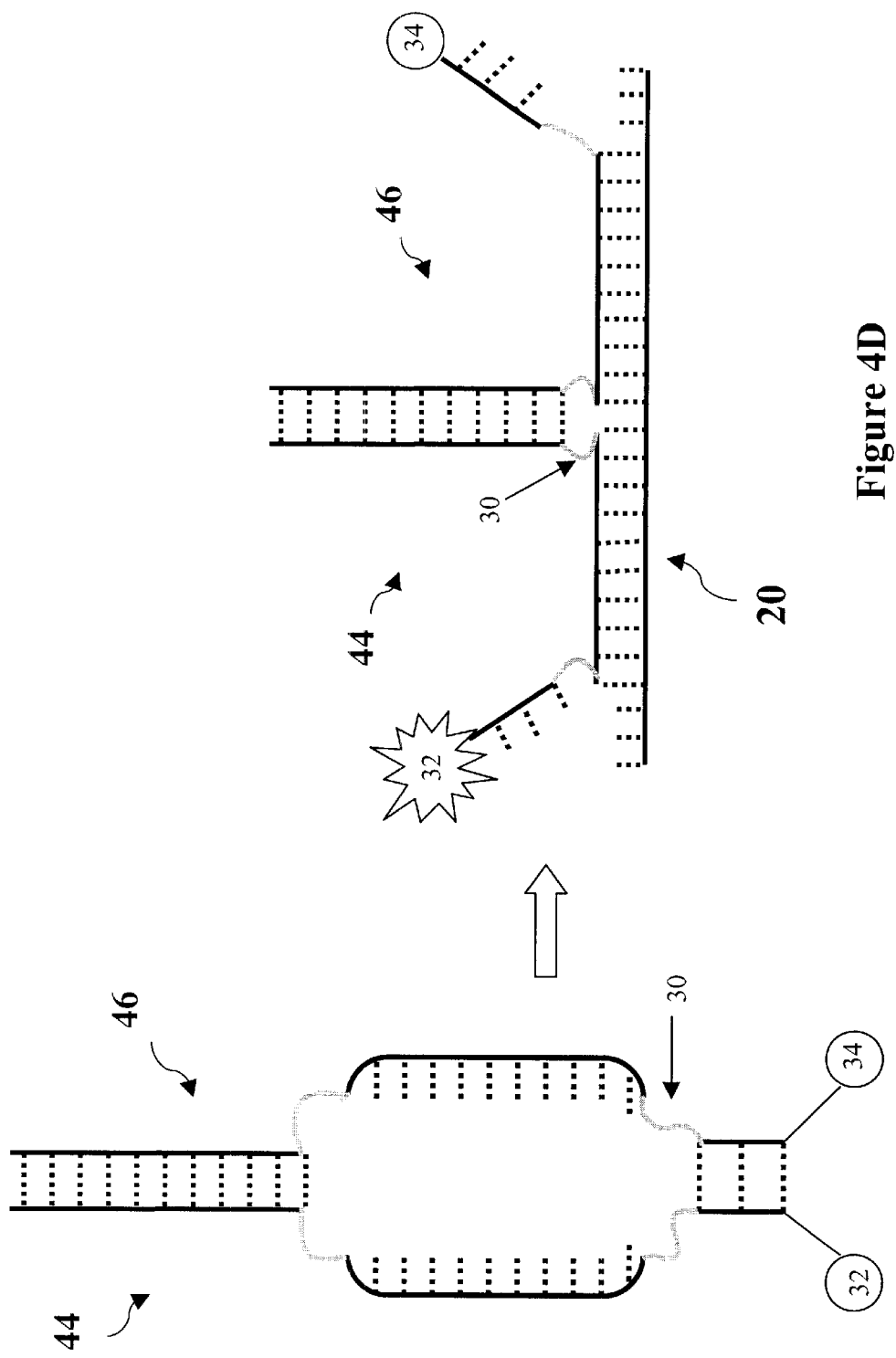

Native PAGE
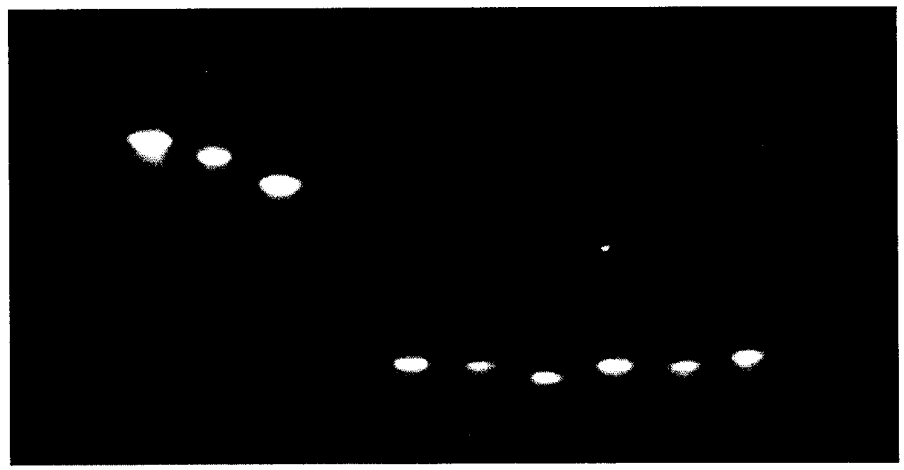
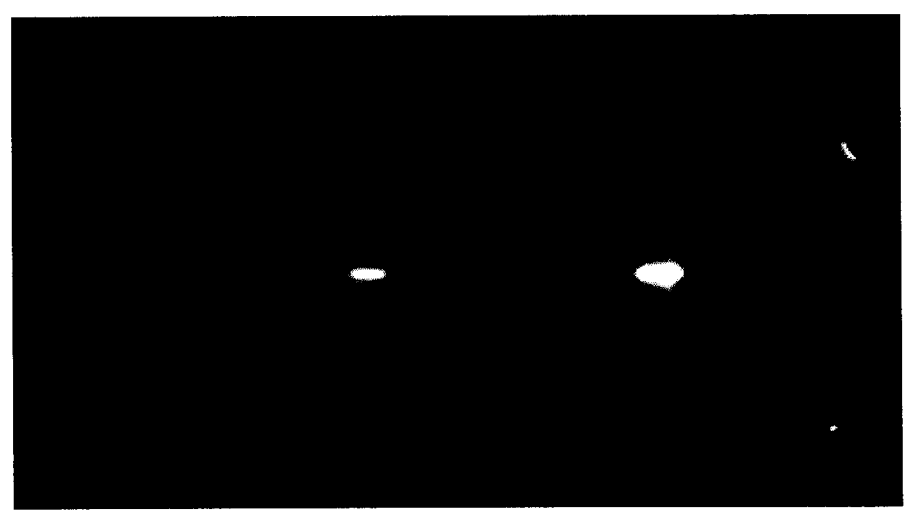
Figure 8

Denaturing PAGE
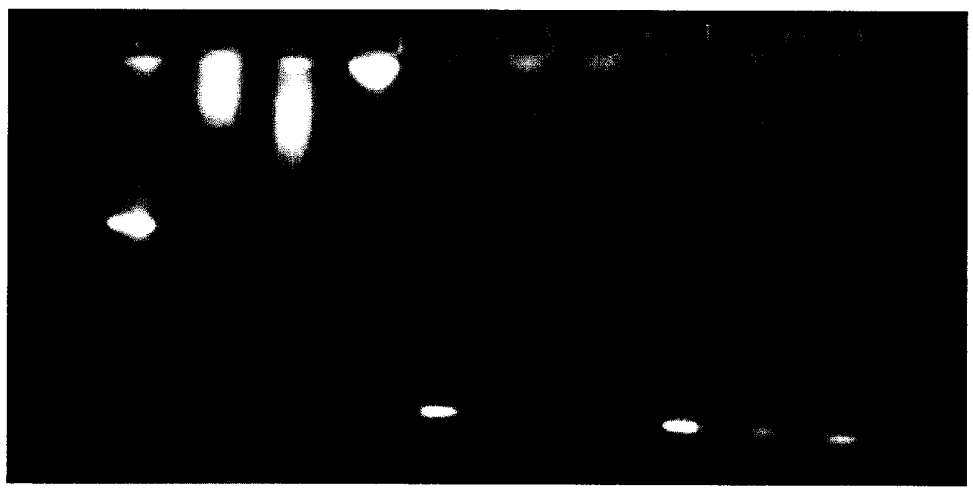
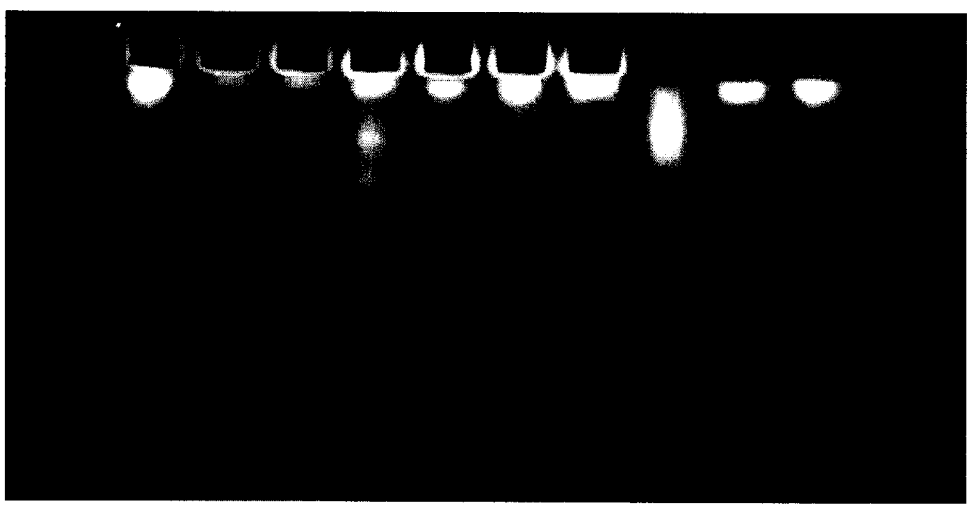
Figure 9

| lane | PNA | PNA | DNA |
|---|---|---|---|
| 1 | ME01 | ME02 | 1057(wt) |
| 2 | ME01 | ME02 | 1059(mut1b) |
| 3 | ME01 | ME02 | 1058(mut3b |
| 4 | ME02 | | 1057 |
| 5 | 1133 | | 1057 |
| 6 | 1133 | | 1059 |
| 7 | 1133 | | 1058 |
| 8 | 1134 | | 1057 |
| 9 | 1134 | | 1059 |
| 10 | 1134 | | 1058 |
| 11 | 1136 | 1137 | 1057 |
| 12 | 1136 | 1137 | 1059 |
| 13 | 1136 | 1137 | 1058 |
| 14 | ME01 | 1137 | 1057 |
| 15 | ME01 | 1137 | 1059 |
| 16 | ME01 | 1137 | 1058 |
| 17 | 1137 | | 1057 |
| 18 | 1136 | ME02 | 1057 |
| 19 | 1136 | ME02 | 1059 |
| 20 | 1136 | ME02 | 1058 |

Figure 10

PNA

| | |
|---|---|
| ME01 | CA GTC AGT-O-CC CAG CC TAT-Lys-Flu |
| ME02 | Rho-O-ATA GCC CAG C-O- ACT GAC TG |
| 1133 | Rho-O-GCC-CAG-C-O-CC-CAG-CC |
| 1134 | Rho-O-GCC-CAG-CCC-CAG-CC |
| 1135 | O-GCC-CAG-C-O-A-CTG-ACT-G |
| 1136 | O-CA-GTC-AGT-O-CC-CAG |
| 1137 | Rho-O-CC-AGC-O-AC-TGA-CTG |

DNA

| | |
|---|---|
| 1057 | GGG CTG GGG CTG GGC AG 3' |
| 1058 | GGG CTG GGG TTT CTG GGC AG 3' |
| 1059 | GGG CTC GGG CTG GGC AG 3' |

SEQUENCE LISTING

<160> NUMBER OF SEQ ID NOS: 3

<210> SEQ ID NO 1
<211> LENGTH: 17
<212> TYPE: DNA
<213> ORGANISM: Unknown
<220> FEATURE:
<223> OTHER INFORMATION: Synthetic DNA

<400> SEQUENCE: 1 gggctgggc tgggcag

```
-continued

<210> SEQ ID NO 2
<211> LENGTH: 20
<212> TYPE: DNA
<213> ORGANISM: Unknown
<220> FEATURE:
<223> OTHER INFORMATION: Synthetic DNA

<400> SEQUENCE: 2
gggctgccct ttctgggcag                                               20

<210> SEQ ID NO 3
<211> LENGTH: 17
<212> TYPE: DNA
<213> ORGANISM: Unknown
<220> FEATURE:
<223> OTHER INFORMATION: Synthetic DNA

<400> SEQUENCE: 3
gggctcgggc tgggcag                                                  17
```

MULTIPARTITE HIGH-AFFINITY NUCLEIC ACID PROBES

I. FIELD OF THE INVENTION

The present invention generally relates to the fields of nucleic acid analogs and hybridization. More specifically, the invention relates to methods and compositions for hybridization of a collection of probes to a target nucleic acid.

II. BACKGROUND

Nucleic acids, such as deoxyribonucleic acid (DNA) and ribonucleic acid (RNA), are bearers of information. This information, encoded in the ordered nucleotides that constitute the nucleic acids, enables a living system to construct a protein, a cell, or an organism. One specific sequence of nucleotides may be found in a virus, whereas a different sequence may be found in a bacterium, and yet a different sequence in a human being. The detection and analysis of nucleic acids has become one of the most fundamental aspects of diagnostic medicine and medical research. Because nucleic acid sequences can also differ among individuals, nucleic acid analysis has also become important to forensic medicine.

Most current methods of nucleic acid analysis require the hybridization of one or more oligonucleotides to a target nucleic acid of interest. The hybridization step is often followed by an enzymatic reaction involving the addition of nucleotides to the hybridized oligonucleotide, as in primer extension reactions or in polymerase chain reactions (PCR). In other cases, the hybridization step is followed by washing and detection steps, as in Southern or Northern blot analysis.

The hybridization of an oligonucleotide to a target nucleic acid generally requires that the sequence of the oligonucleotide be approximately complementary to the sequence of the target nucleic acid. Thus, after the sequence of the target nucleic acid of interest is determined, an appropriate, complementary oligonucleotide for use in hybridization to the target nucleic acid must be designed.

In most cases, the complementary oligonucleotide must be custom-synthesized. Most oligonucleotides used for this purpose are at least twelve nucleotides in length to permit efficient hybridization. Because any of four nucleotides could be present at each position in the oligonucleotide, there are $4^{12}$ or 16,777,216 possible oligonucleotides that are twelve nucleotides in length. The skilled artisan is therefore unlikely to possess, in advance, a newly-desired oligonucleotide. Unfortunately, custom synthesis of oligonucleotides is both expensive and time-consuming: the process may require from 3–6 business days, including ordering, synthesis, and shipping. Inevitably, analysis of the nucleic acids is further delayed.

Thus, because of the importance of nucleic acid analysis to modern medical science, there is a great need for faster, cheaper, and more reliable means to carry out this analysis, such as methods that do not depend on custom-synthesized oligonucleotides. Similarly, there is a need for nucleic acid binding moieties that can be generated rapidly and inexpensively without the impediments of traditional custom synthesis.

III. SUMMARY OF THE INVENTION

It has been discovered that a nucleic acid binding moiety can be generated by combining two or more smaller probes that interact to generate a single binding moiety, also referred to herein as a multipartite binding moiety. For example, if one of the smaller probes includes a portion complementary to a first nucleic acid sequence ("X"), and another of the smaller probes includes a portion complementary to a second nucleic acid sequence ("Y"), then a new, single binding moiety would include a composite nucleic acid recognition sequence complementary to the combination of the first and second regions (X+Y). Accordingly, the invention allows one skilled in the art to create a probe complementary to a target nucleic acid sequence by combining smaller probes, each of which is complementary to a particular subset of the target nucleic acid sequence and is capable of interacting with the other smaller probe(s). This interaction can be achieved, for example, through the formation of a three-way junction.

It has been discovered that a three-way junction can be stabilized by the introduction of a flexible linker between the portion of the smaller probe that interacts with the target nucleic acid and the portion that interacts with the other smaller probe(s). It has also been discovered that the use of peptide nucleic acids or other nucleic acid analogs that interact more strongly with a strand of DNA than would the complementary strand of DNA can improve the affinity of the smaller probes for each other and for the target nucleic acid. Thus, a stable interaction is possible even where each of the smaller probes is complementary only to a small region of the target nucleic acid (e.g. three to eight nucleotides).

One aspect of the invention is a collection of at least two probes for use in hybridizing to a target nucleic acid. In this aspect, a first probe includes a first portion that may be complementary to a first region of a target nucleic acid and capable of hybridizing thereto, joined by a flexible linker to a second portion capable of hybridizing with the second probe. Similarly, the second probe includes a first portion that may be complementary to a second region of the target nucleic acid and capable of hybridizing thereto, and a second portion capable of hybridizing with the first probe. Both the first and second regions of the target nucleic acid typically are from three to eight nucleotides in length, and preferably substantially adjacent, i.e. separated by zero or one nucleotides. Either the first probe or the second probe, or both, is or includes a high-affinity nucleic acid analog. A preferred high-affinity nucleic acid analog is PNA (peptide nucleic acid), where the sugar/phosphate backbone of DNA or RNA has been replaced with a polyamide backbone, e.g. 2-aminoethylglycine.

Because this invention provides a means to generate a larger probe by combining two or more smaller probes, in other embodiments of the invention, the collection of probes includes an array of a plurality of first probes (a library of first probes) and an array of a plurality of second probes (a library of second probes) which may be used to generate a larger probe. In these embodiments, the portion of each of the first probes that may be complementary to the first region of the target nucleic acid has a different sequence, and the portion of each of the second probes that may be complementary to the second region of the target nucleic acid has a different sequence.

The array of first probes often includes at least 50% of the possible combinations of first probes. Thus, if the first region of the target nucleic acid is x nucleotides in length and if the portion of each of the first probes that may be complementary to that region is non-degenerate, the array of first probes includes at least $0.5 \times 4^x$ first probes. Likewise, the array of second probes often includes at least 50% of the possible combinations of second probes.

In other embodiments, the collection of probes is provided in a kit, in combination with a buffer. In one preferred embodiment, the kit also includes an enzyme. In another preferred embodiment, the kit also includes a detection moiety.

Another aspect of the invention is a method of using the collection of probes of the invention. In one embodiment, the invention is a method of detecting the presence of a target nucleic acid sequence. Generally, the target nucleic acid is exposed to the first and second probes to form a complex if the target nucleic acid sequence is present. The presence or absence of the complex may be determined by fluorescent assays, colorimetric assays, enzymatic assays, or by any other means capable of detecting the presence or the absence of the complex. In another embodiment, the exposure and detection steps are iterated using different combinations of first and second probes derived from an array of a plurality of first probes and an array of a plurality of second probes.

In another embodiment, the invention is a method of priming an enzyme-catalyzed reaction such as polymerase chain reaction (PCR), primer extension, ligation, or other amplification methods. In this embodiment, the target nucleic acid is exposed to the first and second probes under conditions that permit the formation of a complex if the target sequence in the target nucleic acid is present. In this embodiment, an enzyme typically is provided to catalyze a reaction primed by the complex.

It should be understood that the order of the steps of the methods of the invention is immaterial so long as the invention remains operable, i.e. permits the formation of a multipartite binding moiety, its association with a target nucleic acid, and any subsequent operations or steps. Moreover, two or more steps may be conducted simultaneously.

The foregoing, and other features and advantages of the invention, as well as the invention itself, will be more fully understood from the following description, drawings, and claims.

BRIEF DESCRIPTION OF THE DRAWINGS

FIG. 1A shows one embodiment of a three-way junction. FIG. 1B shows one embodiment of a four-way junction. FIG. 1C shows one embodiment of a pair of three-way junctions. Solid lines represent target and probe. Dashed lines represent associations, e.g. Watson-Crick base pairing. Gray curved lines are flexible linkers.

FIGS. 2A and 2B show structures of fluorescent dye moieties that may be useful in labelling probes and nucleotides. The attachment site of the dye, X, is linked to a probe or nucleotide.

FIGS. 4A–4D show schematic depictions of probes bearing fluorescent and quenching moieties that may be useful in the practice of one aspect of the invention. In FIGS. 4A and 4B, the fluorescent and quenching moieties are covalently attached to the same probe. In FIGS. 4C and 4D, the fluorescent and quenching moieties are covalently attached to different probes. In FIGS. 4A and 4C, the probe(s) is (are) not associated with a target nucleic acid, and the fluorescent and quenching moieties are in proximity with each other and quenching occurs by FRET. In FIGS. 4B and 4D, the probe(s) is (are) associated with a target nucleic acid in a three-way junction, and the fluorescent and quenching moieties are separated, permitting fluorescence and detection of the complex.

FIG. 8 shows the digitized image of gel electrophoresis (10% polyacrylamide) conducted under native, non-denaturing conditions, i.e. room temperature and no urea. Fluorescence detection.

FIG. 9 shows the digitized image of gel electrophoresis (10% polyacrylamide) of the same samples as FIG. 8, conducted under denaturing conditions, i.e. 35° C. and 7M urea. Fluorescence detection.

FIG. 10 shows the PNA probes and DNA oligonucleotides used in the multipartite and control complex analyses in each lane of FIGS. 8 and 9.

FIG. 11 shows the sequences of the PNA probes and DNA oligonucleotides used in the multipartite and control complex analyses in each lane of FIGS. 8 and 9. Flu -carboxyfluorescein. Rho-tetramethylrhodamine (TAMRA). O-O linker, linker (2-[2-(2- aminoethoxy]acetic acid.

DETAILED DESCRIPTION OF PREFERRED EMBODIMENTS

V.1. Definitions

Figure 1A:
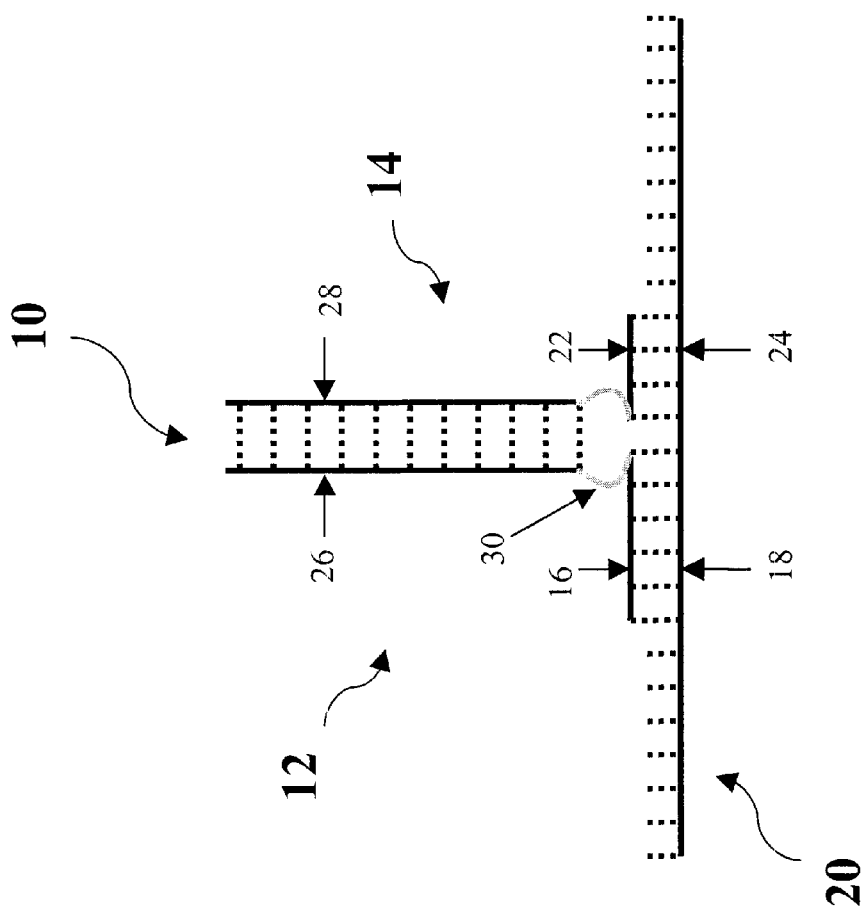
FIGS. 1A–1C show schematic depictions of multipartite binding moieties hybridizing to target nucleic acids.

As used herein, "nucleic acid" encompasses the terms oligonucleotide and polynucleotide and denotes single stranded and double-stranded polymers of nucleotide monomers, including 2'-deoxyribonucleotides (DNA) and ribonucleotides (RNA). The nucleic acid may be composed entirely of deoxyribonucleotides, entirely of ribonucleotides, or chimeric mixtures thereof. The monomers are typically linked by internucleotide phosphodiester bond linkages, and associated counterions, e.g., $H^+$, $NH_4^+$, trialkylammonium, $Mg^{2+}$, and $Na^+$. Nucleic acids typically range in size from a few monomeric units, e.g., 5'40, when they are commonly referred to as oligonucleotides, to several thousands of monomeric units. Whenever an oligonucleotide sequence is represented, it will be understood that the nucleotides are in 5'to 3'order from left to right and that "A" denotes deoxyadenosine, "C" denotes deoxycytidine, "G" denotes deoxyguanosine, and "T" denotes thymidine, unless otherwise noted.

As used herein, "nucleic acid analog" is understood to mean a structural analog of DNA or RNA, designed to hybridize to complementary nucleic acid sequences (Hunziker, J. and Leumann, C. (1995) "Nucleic Acid Analogues: Synthesis and Properties" in *Modern Synthetic Methods*, Vol. 7, pp. 331–417). Through modification of the internucleotide linkage(s), the sugar, and/or the nucleobase, nucleic acid analogs may attain any or all of the following desired properties: 1) optimized hybridization specificity or affinity, 2) nuclease resistance, 3) chemical stability, 4) solubility, 5) membrane-permeability, and 6) ease or low costs of synthesis and purification. Examples of nucleic acid analogs include, but are not limited to, peptide nucleic acids (PNA), locked nucleic acids "LNA" (Imanishi, etal WO 98/39352; Imanishi, etal WO 98/22489; Wengel, etal WO 00/14226), 2'-O-methyl nucleic acids (Ohtsuka, etal, U.S. Pat. No. 5,013,830), 2'-fluoro nucleic acids, phosphorothioates, and metal phosphonates.

The term "target nucleic acid" are capable of hybridizing with the probes of the invention and include genomic DNA, DNA digests, plasmids, vectors, viral DNA, PCR products, RNA, and synthetic nucleic acids. Target nucleic acid may also be a metaphase or interphase chromosome. Target nucleic acids may be single-stranded or double-stranded and can range from as few as about 20–30 nt to as many as millions of nucleotides (nt) or base-pairs (bp), depending on the particular application. "Target sequence" means a polynucleotide sequence that is the subject of hybridization with a complementary polynucleotide, e.g. a primer or probe. The sequence can be composed of DNA, RNA, an analog thereof, including combinations thereof. The terms "target region", "target sequence", and "target nucleic acid sequence" mean a region of a nucleic acid which is to be detected.

As used herein, "high-affinity nucleic acid analog" is understood to mean a nucleic acid analog with a higher binding affinity for a strand of DNA than the corresponding complementary strand of DNA. Examples include PNA, LNA, 2'-O-methyl nucleic acids, and 2'-fluoro nucleic acids. Examples of nucleic acid analogs also include chimera molecules comprising one or more nucleic acid analog units and one or more DNA (2'-deoxynucleotide) units. For example, a nucleic acid analog may be a PNA-DNA chimera comprised of a PNA moiety and a DNA moiety.

As used herein, "PNA" or "peptide nucleic acid" is understood to mean a high-affinity nucleic acid analog in which the sugar/phosphate backbone of DNA or RNA has been replaced with a polyamide-based backbone.

As used herein, "flexible linker" is understood to mean a region of a probe that is conformationally more flexible than a strand of DNA. Preferably, a flexible linker minimizes strain in a three-way or higher-order junction. Appropriate flexible linkers include, but are not limited to, ethyleneoxy units and alkyldiyl. "Detection moiety" means a label enabling the detection of a complex. Preferably, the detection moiety permits the direct detection of the complex. Detection moieties include, but are not limited to, fluorescent moieties, enzymatic moieties, or moieties comprising a defined antigen (e.g., a hemagluttinin tag, a myc tag, or the like). "Destabilizing moiety" means a label, functional group or other modification to one or more of the probes in a multipartite complex that effectively decreases the melting temperature of the complex formed by the coming together of two or more probes, typically by destabilizing base pairing and hydrogen bonding as usually occurs when complementary strands of nucleic acids become hybridized.

"Probe" means a nucleic acid or nucleic acid analog which is useful for hybridization to a target nucleic acid. For example, a probe may be a first nucleic acid or nucleic acid analog connected to a second nucleic acid or nucleic acid analog by a flexible linker. A probe may optionally include a detectable moiety.

As used herein, "substantially adjacent" describes two regions of a nucleic acid that are separated by zero or one intervening nucleotides.

As used herein, a "universal" nucleobase is understood to mean a nucleobase that does not discriminate among cytosine, guanine, adenine, thymine, and uracil. Universal nucleobases include, for example, xanthine and 5-nitropyrole (Nature (1994) 369:492–493).

As used herein, "degeneracy" is understood to mean the number of naturally-occurring nucleotide sequences to which a given probe is complementary. Thus, a non-degenerate probe has a degeneracy of one, whereas a probe with one universal nucleobase has a degeneracy of four, and a probe with two universal nucleobases has a degeneracy of sixteen.

V.2. Structure of the Probes—a First Portion for Binding to a Target Nucleic Acid A multipartite nucleic acid binding moiety is formed by the combination of at least two smaller probes, each of which can interact both directly with a target nucleic acid and directly or indirectly with each other. The binding moiety can interact with a target nucleic acid, and the specificity of the binding moiety for the target nucleic acid is determined by the combined specificities of certain sequences of the smaller probes that form the binding moiety. Thus, the skilled artisan can rapidly generate a binding moiety complementary to a particular target nucleic acid by judiciously selecting smaller probes and combining them to form a single binding moiety. This invention therefore facilitates and accelerates nucleic acid analysis and is effective to save time and money in medical research, diagnostic medicine, forensic medicine, and in all other branches of biology and medicine requiring the study of nucleic acids.

The invention relates to a binding moiety composed of at least two probes. Each probe comprises a first portion that may be complementary to a region of a target nucleic acid and capable of hybridizing thereto. For example, the binding moiety 10 in FIG. 1A is composed of a first probe 12 and a second probe 14. The first probe 12 contains a first portion 16 complementary to a first region 18 of the target nucleic acid 20. Similarly, the second probe 14 contains a first portion 22 complementary to a second region 24 of the target nucleic acid 20. The first portions 16 and 22 include a nucleic acid, nucleic acid analog, or a chimera thereof. The presence of a nucleic acid in at least one of the first portions 16 and 22 is preferred in some embodiments, particularly where binding of the probes to the target nucleic acid 20 is followed by an enzymatic reaction as discussed below. The first probe and/or the second probe comprise a high-affinity nucleic acid analog. The binding moiety 10 and target 20 may form a three-way junction, as shown in FIG. 1A. Three-way junctions and higher-order nucleic acid complexes have been studied. See for example: Duckett etal (1990) EMBO Journal, 9:1659–64; Leontis etal (1993) J. Biomol. Structure & Dynamics, 11:215–23; Rosen etal (1993) Biochemistry, 32:6563–87; Shlyakhtenko etal (1994) J. Biomol. Structure & Dynamics, 12:131–43; Husler etal (1995) Arch. of Biochemistry and Biophysics 322:149–66; Welch etal (1995) J. Mol. Biol. 251:507–19; Yang etal (1996) Biochemistry 35:7959–67.

In most embodiments, the presence of a high-affinity nucleic acid analog in at least one of the first portions 16 and 22 is preferred. In a more preferred embodiment, each of the first portions includes a high-affinity nucleic acid analog. A particularly preferred high-affinity nucleic acid analog is PNA. For example, PNA in which the sugar/phosphate backbone of DNA or RNA has been replaced with 2-aminoethylglycine demonstrates exceptional hybridization specificity and affinity when nucleobases are attached to the linkage through an amide bond (WO 92/20702; P. Nielsen etal., "Sequence-selective recognition of DNA by strand displacement with a thymidine-substituted polyamide," Science (1991) 254:1497–1500). Synthesis of PNA can be conducted by any method known in the art (U.S. Pat. Nos. 5,539,082, 5,714,331, 5,786,461; also WO 93/12129).

2-Aminoethylglycine PNA oligomers typically have greater affinity, i.e. hybridization strength and duplex stability, for their complementary PNA, DNA, and RNA than the corresponding DNA sequences (U.S. Pat. No. 5,985,563; WO 98/24933; WO 99/22018; WO 99/21881; WO 99/49293). The melting temperatures ($T_m$) of PNA/DNA and PNA/RNA hybrids are higher than those of the corresponding DNA/DNA or DNA/RNA duplexes (generally 1° C. per bp) due to a lack of electrostatic repulsion in the PNA-containing complexes. Also, unlike DNA/DNA duplexes, the $T_m$ of PNA/DNA duplexes are largely independent of salt concentration.

2-Aminoethylglycine PNA oligomers also demonstrate a high degree of base-discrimination (specificity) in pairing with their complementary strand. Specificity of hybridization can be measured by comparing $T_m$ values of duplexes having perfect Watson/Crick complementarity with those having one or more mismatches. The degree of destabilization of mismatches, measured by the decrease in $T_m$ ($\Delta T_m$), is a measure of specificity. In addition to mismatches, specificity and affinity are affected by structural modifications, hybridization conditions, and other experimental parameters (Egholm, etal (1993) Nature 365:566–68).

Thus, by including PNA or other high-affinity nucleic acid analogs in first portion(s) 16 and/or 22, specificity of binding is maintained or increased, and the affinity for the target is increased. Thus, use of PNA or other high-affinity nucleic acid analogs permits the use of smaller first portions of probes without sacrificing affinity. For example, whereas a DNA oligonucleotide might require binding to 15 or more nucleotides of a target nucleic acid for stable interaction, a PNA may require binding to less than 15 nucleotides under the same conditions. Preferably, neither the first probe 12 nor the second probe 14 contains a destabilizing moiety (Weston etal, WO 99/37806).

Accordingly, in a preferred embodiment, a first portion 16 of a first probe 12 is complementary to a first region 18 of from about 3 to 8 nucleotides in length. As shown as an example in FIG. 1A, first portion 16 binds to a six nucleotide first region 18 of target 20.

Preferably, the first portion 22 of a second probe 14 is complementary to a second region 24 of from 3 to 8 nucleotides in length. More preferably, the second region 24 is from five to seven nucleotides in length. In another preferred embodiment, the combined lengths of the first and second regions are from 6 to 12 nucleotides.

The neutral backbone of PNA also increases the rate of hybridization significantly in assays where either the target, template, or the PNA probe is immobilized on a solid substrate. Without any electrostatic repulsion, the rate of hybridization is often much higher for PNA probes than for DNA or RNA probes in applications such as Southern blotting, Northern blots, or in situ hybridization experiments (D. Corey, (1995) "48,000-fold acceleration of hybridization by chemically modified oligonucleotides," J. Amer. Chem. Soc. 117:9373–74).

With certain DNA sequences, a second PNA can further bind to form an unusually stable triple helix structure (PNA)$_2$/DNA. PNA have been investigated as potential antisense agents, based on their sequence-specific inhibition of transcription and translation (Lee etal, (1998) Biochemistry 37:900–10; Nielsen, P. (1996) Antisense Therapeutics 4:76–84). However, PNA oligomers themselves are not substrates for a polymerase as primers or templates, and do not conduct primer extension with nucleotides (U.S. Pat. No. 5,629,178).

Accordingly, if primer extension or similar enzyme-catalyzed reactions are to follow binding of the probes to a target nucleic acid, at least one of the probes preferably includes a PNA-DNA chimera with a 3' hydroxyl. PNA-DNA chimeras are oligomer molecules with discrete PNA and nucleotide moieties. They can be synthesized by covalently linking PNA monomers and nucleotides in virtually any combination or sequence. Efficient and automated methods have been developed for synthesizing PNA-DNA chimeras (Vinayak etal., (1997) Nucleosides & Nucleotides 16:1653–56; Uhlmann etal (1996) Angew. Chem., Intl. Ed. Eng. 35:2632–35; Van der Laan etal, (1997) Tetrahedron Lett. 38:2249–52; U.S. Pat. No. 6,063,569). PNA-DNA chimeras are designed to have desirable properties found in PNA and DNA, e.g. superior hybridization properties of PNA and biological functions like DNA (E. Uhlmann (1998) Biol. Chem. 379:1045–52).

V.3 Structure of the Probes—a Second Portion for Binding to the Other Probe(s)

Figure 1B:
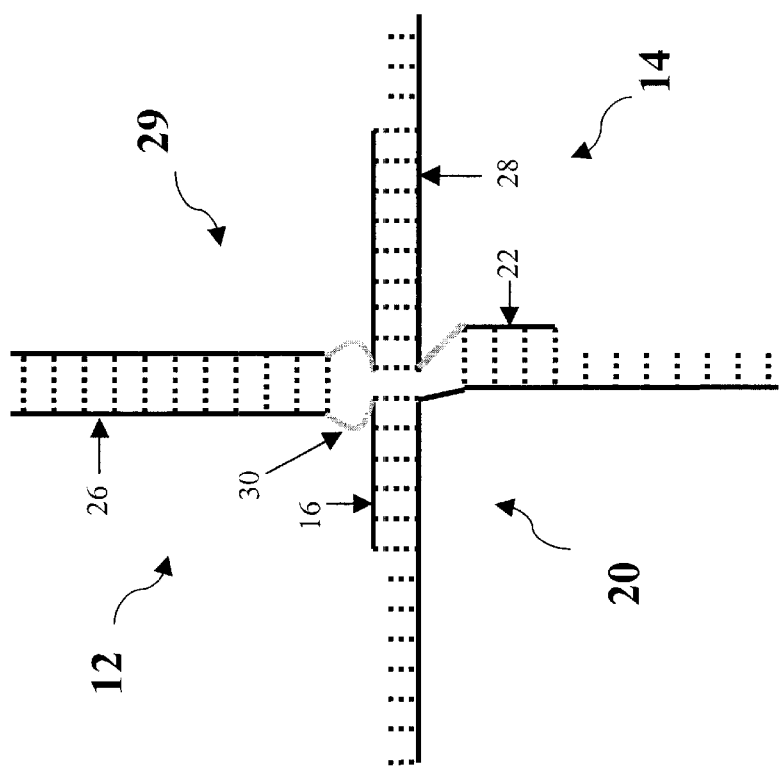

The first probe also includes a second portion capable of hybridizing, directly or indirectly, with a second portion of a second probe. In the preferred embodiment depicted in FIG. 1A, the association between the second portion 26 of the first probe 12 and the second portion 28 of the second probe 14 is a direct association by hybridization. In other embodiments, the association between the second portions 26 and 28 is indirect. In these embodiments, one or more bridging molecules may connect the second portions of the probes. For example, as shown in FIG. 1B, a bridging probe 29 hybridizes simultaneously with second portion 26 and second portion 28 to form a four-way junction. Alternatively, a bridging probe could associate simultaneously with second portion 26 and with a second bridging probe capable of hybridizing with second portion 28. In preferred embodiments, however, the association between second portion 26 and second portion 28 is direct.

Both second portion 26 and second portion 28 preferably include a nucleic acid and/or a nucleic acid analog. In more preferred embodiments, both second portion 26 and second portion 28 include a high-affinity nucleic acid analog such as PNA. Because PNA-PNA duplexes are more stable than PNA-DNA duplexes, as discussed above, use of PNA favors the (appropriate) association of the probes with each other rather than an (inappropriate) interaction between the second portions of the probes and, for example, the target nucleic acid. Inappropriate interactions between the second portions of the probes and the target nucleic acid can be further disfavored by the use of sequences that are not complementary to natural nucleic acids. For example, the use of isocytosine-isoguanine base pairs between the second portions of the probes would strongly disfavor inappropriate direct interaction between a second portion and a natural target nucleic acid because naturally-occurring sequences do not comprise isocytosine or isoguanine and the isocytosine or isoguanine base pair is highly specific (U.S. Pat. Nos. 5,432,272 and 6,001,983; Tetrahedron Letters 36:3601–04).

Other non-natural nucleobases could be used to the same effect (Fasman (1989) *Practical Handbook of Biochemistry and Molecular Biology*, pp. 385–394, CRC Press, Boca Raton, Fla., as could other means to induce a specific interaction, e.g. ligand-receptor, antigen-antibody, and the like.

In most embodiments, the association occurs through noncovalent chemical interactions, such as hydrogen bonds (e.g. Watson-Crick or Hoogsteen-type base pairing), ionic bonds, and/or hydrophobic forces. Although the probes are associated with each other when they are associated with the target nucleic acid, in preferred embodiments they are also associated with each other in solution in the absence of a target nucleic acid. It is understood that the association of the probes will be affected by environmental factors. These factors may include, for example, temperature, pH, ionic concentrations, and a variety of other agents and factors well known in the art that influence hybridization. The practice of this invention requires only that the probes comprise a chemical moiety that promotes the interaction of the probes. By virtue of this tendency to associate, the binding of the probes to a target nucleic acid is rendered cooperative.

V.4 Structure of the Probes—a Flexible Linker Joining the First and Second Portions The first and second portions of the first probe are typically joined by a flexible linker. In certain embodiments, a probe may not require a flexible linker. In the preferred embodiment depicted in FIG. 1A, the first portion 16 and the second portion 26 of first probe 12 are joined by flexible linker 30. In this preferred embodiment, the first portion 22 and second portion 28 of second probe 14 are also separated by a flexible linker 30. The flexible linker typically is a multi-atom linker. The linker may optionally include one or more heteroatoms, an O-linker, and/or one or more ethyleneoxy units, —(CH$_2$CH$_2$O)—. Flexible linkers containing ethyleneoxy units are preferred where there are up to six ethyleneoxy units. Ethyleneoxy linkage units can be linked to PNA or DNA moieties, for example, through amide or phosphate bonds. Ethyleneoxy linkage units can be installed by methods known in the art, for example, using coupling reagents such as protected forms of 2-[2-(2-aminoethoxy)ethoxy]acetic acid. The O-linker, 2-[2-(2-aminoethoxy)ethoxy]acetic acid, may be coupled as the FMOC-amino protected amide-forming carboxylic acid, or phosphoramidite synthons. One or more O-linker units act as a flexible, non-base pairing linkage between the first and second portions of the probe. The flexible linker may also be, for example, an alkyldiyl consisting of 1 to 20 carbon atoms, such as hexyldiyl (U.S. Pat. No. 5,281,701). The linker could also be an aryldiyl consisting of 6 to 20 carbon atoms, such as 1,4-phenyldiyl.

V.5 Structure of the Probes—Labeling Moieties

One or more of the probes may optionally include a detectable label. In one embodiment, one or more of the probes is directly or indirectly associated with an enzyme having a detectable activity. In another embodiment, one or more of the probes comprises a moiety that can specifically bind a detectable target. For example, a probe could comprise a biotin moiety, capable of specific binding to a detectably-labeled avidin. Alternatively, a probe could comprise an antigen, capable of specific binding to a detectable antibody. In a preferred embodiment, one probe comprises a fluorescent dye moiety, and one probe comprises a quenching moiety.

Labeling can be accomplished using any one of a large number of known techniques employing known labels, linkages, linking groups, reagents, reaction conditions, and analysis and purification methods. Nucleic acids and nucleic acid analogs can be labeled at sites including a nucleobase, a sugar, the aminoethylglycine backbone, an amino residue, a sulfide residue, a hydroxyl residue, or a carboxyl residue. Nucleobase label sites include the deaza C-7 or C-8 positions of the purine and the C-5 position of the pyrimidines. Preferably, the linkage between the label and the nucleic acid or nucleic acid analog is an acetylenic amido or alkenic amido linkage (U.S. Pat. Nos. 5,770,716 and 5,821,356). A linker can also comprise an alkyldiyl, aryldiyl, or ethyleneoxy unit. Typically, a carboxyl group on the label is activated by forming an active ester, e.g., N-hydroxysuccinimide ester, and reacted with an amino group on the aminoethyleneoxy-, alkynylamino- or alkenylamino-derivatized nucleic acid or nucleic acid analog. Preferably, the nucleic acid or nucleic acid analog is an aminoethyleneoxy derivative.

A nucleobase-labelled oligonucleotide may have the following formula:

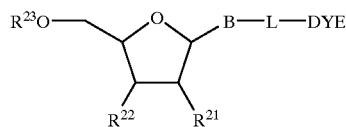

where the oligonucleotide comprises 2 to 100 nucleotides. DYE is a fluorescent dye, including energy transfer dye. B is a nucleobase, e.g. uracil, thymine, cytosine, adenine, 7-deazaadenine, guanine, and 8-deazaguanosine. L is a linker. $R^{21}$ is H, OH, halide, azide, amine, $C_1$–$C_6$ aminoalkyl, $C_1$–$C_6$ alkyl, allyl, $C_1$14 $C_6$ alkoxy, OCH$_3$, or OCH$_2$CH=CH$_2$. $R^{22}$ is H, phosphate, internucleotide phosphodiester, or internucleotide analog. $R^{23}$ is H, phosphate, internucleotide phosphodiester, or internucleotide analog. In this embodiment, the nucleobase-labelled oligonucleotide may bear multiple fluorescent labels, e.g. dyes, attached through the nucleobases. Nucleobase-labelled oligonucleotides may be formed by: (i) enzymatic incorporation of enzymatically incorporatable nucleotide reagents where $R^{19}$ is triphosphate, by a DNA polymerase or ligase, and (ii) coupling of a nucleoside phosphoramidite reagent by automated synthesis. Whereas, nucleobase-labelled oligonucleotides may be multiply labelled by incorporation of more than one incorporatable nucleotide, labelling with a phosphoramidite dye label reagent leads to singly 5'-labelled oligonucleotides, according to the following formula:

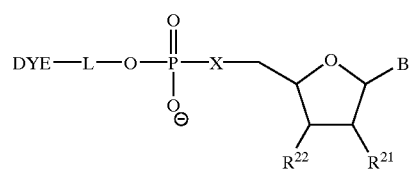

where X is O, NH, or S; $R^{21}$ is H, OH, halide, azide, amine, $C_1$–$C_6$ aminoalkyl, $C_1$–$C_6$ alkyl, allyl, $C_1$–$C_6$ alkoxy, OCH$_3$, or OCH$_2$CH=CH$_2$; $R^{22}$ is H, phosphate, internucleotide phosphodiester, or internucleotide analog; and $R^{23}$ is H, phosphate, internucleotide phosphodiester, or internucleotide analog. L is alkyldiyl, aryldiyl, or polyethyleneoxy.

Preferably, L is n-hexyldiyl.

A preferred class of labels provides a signal for detection of labeled extension products by fluorescence, chemiluminescence, and electrochemical luminescence. Particularly preferred chemiluminescent labels are 1,2-dioxetane compounds. Useful fluorescent dyes include fluoresceins, rhodamines, cyanines, and metal porphyrin complexes.

Figure 2B:
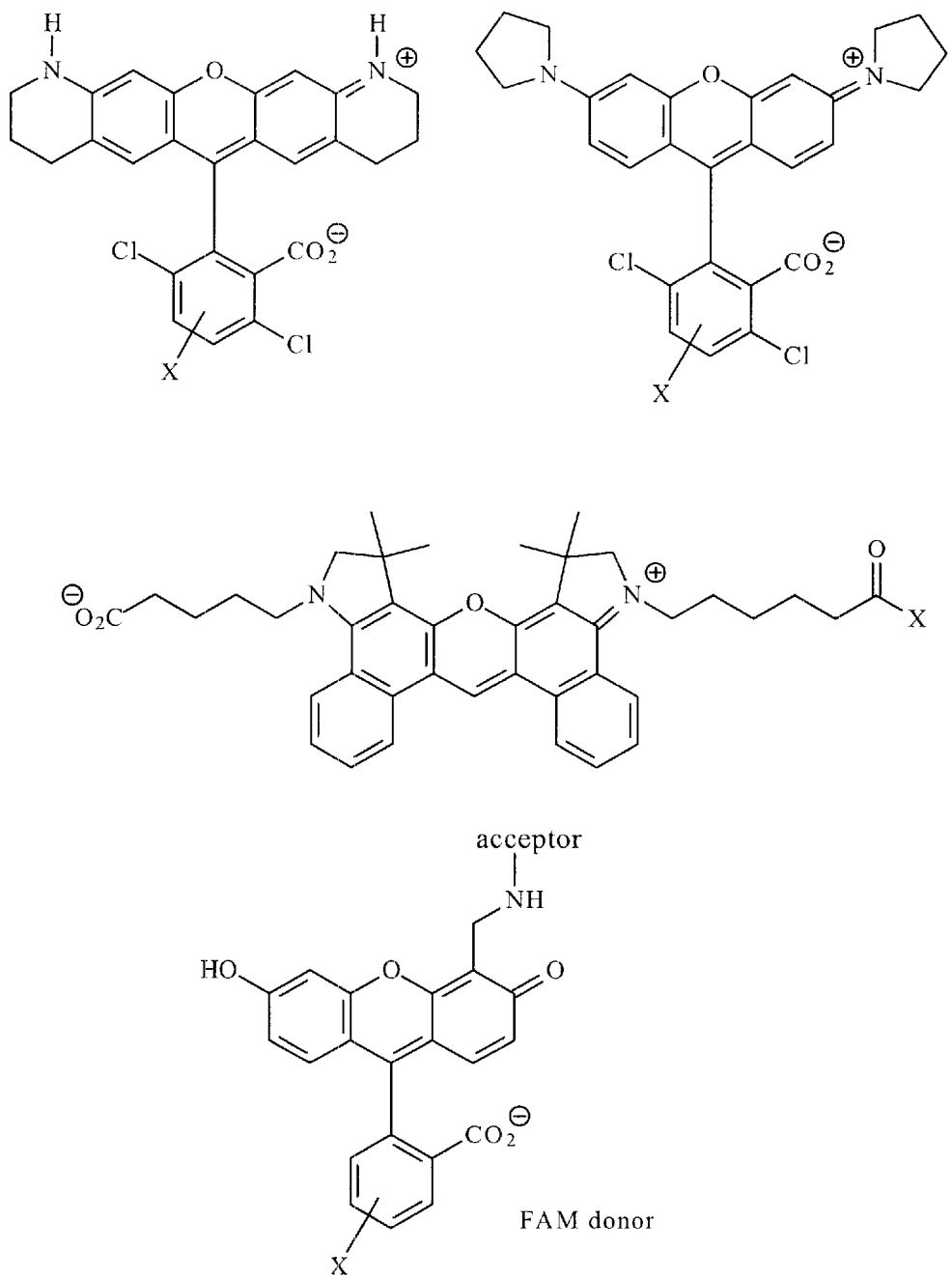

Examples of fluorescein dyes include those shown in FIGS. 2A and 2B (U.S. Pat. Nos. 5,366,860; 5,840,999; 6,008,379; 6,020,481; 5,936,087 and 6,051,719). The 5-carboxyl, and other regio-isomers, may also have useful detection properties. Fluorescein and rhodamine dyes with 1,4-dichloro substituents (bottom ring as shown) are especially preferred (U.S. Pat. Nos. 5,188,934; 5,654,442; 5,885,778; 5,847,162; 6,025,505).

Another preferred class of labels includes fluorescence quenchers. The emission spectrum of a quencher overlaps with a proximal intramolecular or intermolecular fluorescent dye such that the fluorescence of the fluorescent dye is substantially diminished or quenched by the phenomenon of fluorescence resonance energy transfer (FRET).

Figure 3:
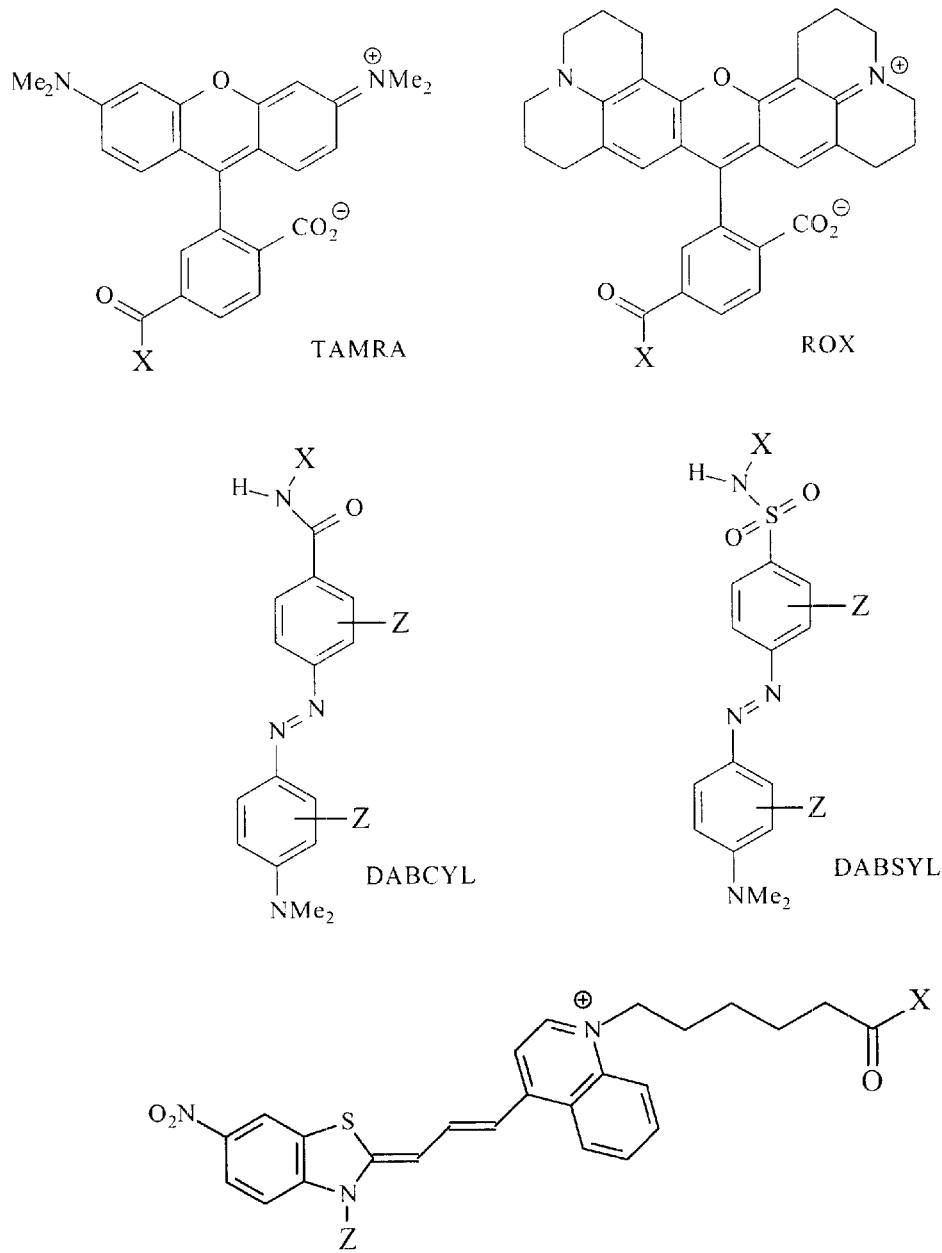
FIG. 3 shows structures of quenching moieties that may be useful in FRET labelling of probes. Substituents Z may be alkyl, aryl, or functional group. The attachment site of the quencher, X, is linked to a probe or nucleotide.

Particularly preferred quenchers include, but are not limited to, rhodamine fluorescent dyes including tetramethyl-6-carboxyrhodamine (TAMRA), tetrapropano-6-carboxyrhodamine (ROX), and DABSYL, DABCYL, asymmetric cyanines (U.S. Pat. No. 6,080,868), anthraquinone, malachite green, nitrothiazole, and nitroimidazole compounds and the like (FIG. 3). Nitro-substituted forms of quenchers are especially preferred.

Energy-transfer dyes are another preferred class of oligonucleotide labels. An energy-transfer dye label includes a donor dye linked to an acceptor dye or an intramolecular FRET pair (FIG. 2B). Light, e.g., from a laser, at a first wavelength is absorbed by a donor dye. The donor dye emits excitation energy absorbed by the acceptor dye. The acceptor dye fluoresces at a second wavelength, with an emission maximum preferably about 100 nm greater than the absorbance maximum of the donor dye.

The donor dye and acceptor dye of an energy-transfer label may be directly attached by a linkage such as one formed from an aminomethyl group at the 4' or 5' position of a donor dye and a 5- or 6- carboxyl group of an acceptor dye (FIG. 3B). Other rigid and non-rigid linkers may be useful.

Oligonucleotides that are intramolecularly labelled with both fluorescent dye and quencher moieties are useful in nucleic acid hybridization assays, e.g. the "Taqman™" exonuclease-cleavage PCR assay (U.S. Pat. Nos. 5,538,848 and 5,723,591). In a Taqman™-type assay, the probe is self-quenching, containing fluorescent dye and quencher moieties. Spectral overlap allows for efficient energy transfer (FRET) when the probe is intact (Clegg, R. "Fluorescence resonance energy transfer and nucleic acids", (1992) Meth. Enzymol, 211:353–388). When hybridized to a target, the probe is cleaved during PCR to release a fluorescent signal that is proportional to the amount of target-probe hybrid present.

In one preferred embodiment depicted in FIGS. 4A and 4B, a first probe 40 comprises a fluorescent moiety 32 near one end and a quenching moiety 34 near the other end. In this embodiment, a small region of complementarity near the ends of the probe promotes the formation of a hairpin loop in the probe when the first probe is not associated with a target nucleic acid, as depicted in FIG. 4A. The hairpin loop brings the quenching moiety 34 into proximity with the fluorescent moiety 32, quenching its fluorescence. When the probe participates in a complex with a second probe 42 to form a three-way junction with a target nucleic acid, the quenching moiety 34 is separated from the fluorescent moiety 32, leading to fluorescence of the label.

A more preferred embodiment is depicted in FIGS. 4C and 4D. In this embodiment, one probe 44 comprises a fluorescent moiety 32 near the end comprising the portion that may be complementary to a target nucleic acid, and a second probe 46 comprises a quenching moiety 34 near the end comprising the portion that may be complementary to a target nucleic acid. In the absence of the target nucleic acid, the fluorescent moiety 32 and the quenching moiety 34 are held in proximity by a small region of complementarity as shown in FIG. 4C. In the presence of the target nucleic acid, the fluorescent moiety 32 and quenching moiety 34 are separated, permitting fluorescence and detection of the complex.

In certain embodiments, different probes are labelled with different, independently detectable labels, such as fluorescent dyes having spectrally-resolvable emission spectra to allow the simultaneous detection of a plurality of target nucleic acid sequences. Such multi-label systems are advantageous in applications requiring analysis of multiple probe experiments. In such systems when the labels are fluorescent dyes, each dye can be identified by spectral resolution, enabling multiple target identification (U.S. Pat. Nos. 5,188,934; 5,366,860; and 5,538,848).

V.6 Association With a Target Nucleic Acid

The target nucleic acid can be any nucleic acid or nucleic acid analog capable of hybridizing to a primer or probe, or capable of mediating template-directed nucleic acid synthesis. As shown in the preferred embodiment in FIG. 1A, the binding moiety 10 contacts the target nucleic acid 20 through the first portions 16 and 22 of the first and second probes, 12 and 14, respectively. It should be noted that the first portions 16 and 22 can associate with the same strand of the target nucleic acid 20, as shown in FIG. 1A.

Where a first portion 16 or 22 includes PNA, the PNA should be oriented to permit an essentially antiparallel conformation between the nucleic acid of the first portion and the target nucleic acid 20. The anti-parallel orientation (where the carboxyl terminus of PNA is aligned with the 5' terminus of the nucleic acid, and the amino terminus of PNA is aligned with the 3' terminus of the nucleic acid) is preferred because the resulting complex is typically more stable (M. Egholm etal., (1993) "PNA hybridizes to complementary oligonucleotides obeying the Watson-Crick hydrogen bonding rules," Nature 365:566–68).

In one preferred embodiment, the binding of the probes to the target nucleic acid leads to the formation of a three-way junction. As depicted in FIG. 1A, the flexible linker 30 of first probe 12 helps to alleviate the strain associated with the three-way junction structure. The flexible linker 30 of second probe 14, if present, also helps to alleviate the strain associated with the complex.

In a preferred embodiment, the first region 18 and the second region 24 of the target nucleic acid 20 are substantially adjacent, i.e. separated by zero or one nucleotides. This permits cooperativity from favorable base-stacking interactions in addition to the cooperativity derived from the interaction between the second portions of the probes (Kandimalla etal (1995) Nucleic Acids Res. 23: 3578–84).

In a particularly preferred embodiment, the binding moiety includes two PNA probes, each of which includes a flexible linker, and the binding moiety binds to a target nucleic acid to form a three-way junction. It has been discovered that, in this embodiment, efficient hybridization is possible where one probe is complementary to a five nucleotide region of a target nucleic acid and the other probe is complementary to a seven nucleotide region. Thus, in a preferred embodiment, one probe comprises a first portion that may be complementary to a five nucleotide region of a target nucleic acid, and a second probe comprises a first portion that may be complementary to a seven nucleotide region of a target nucleic acid. In another preferred embodiment, each of two probes comprises a first portion that may be complementary to a six nucleotide region of a target nucleic acid. However, it should be understood that smaller or larger nucleotide regions may be encompassed by the invention.

Figure 1C:
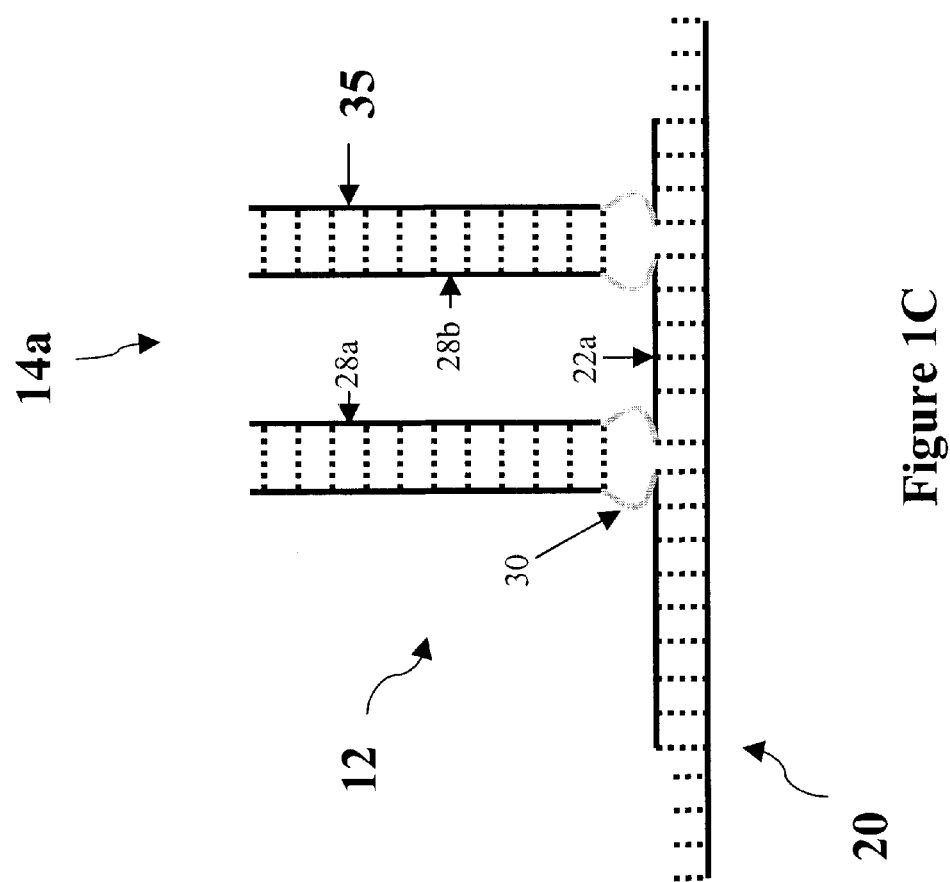

The skilled artisan will appreciate that the invention is not limited to structures containing three-way junctions. Complexes comprising various bridging molecules could form a four-way junction as shown in FIG. 1B, a five-way junction, or another higher-order complex. One or more triple helices (Kandimalla, etal (1995) Nucleic Acids Res. 23:4510–17; Kandimalla, etal (1995) Nucleic Acids Res. 23:1068–74) could be included in the complex, as could a variety of double-helical conformations, such as those resembling A-DNA, B-DNA, or Z-DNA. Additionally, the above elements may be combined in any operable combination. For example, one embodiment of the invention is a structure with two three-way junctions as shown in FIG. 1C. In this embodiment, a first probe 12 and a second probe 14a form a three-way junction with the target nucleic acid 20, and the second probe 14a and a third probe 35 also form a three-way junction with the target nucleic acid 20. In this embodiment, the second probe 14a includes at least three portions: a first portion 28a capable of hybridizing with the first probe, a second portion 22a capable of hybridizing with the target nucleic acid, and a third portion 28b capable of hybridizing with the third probe. Many other geometries are similarly envisioned. Only two elements of the geometry are required: first, that at least two probes interact directly or indirectly through their second portions 26 and 28; and second, that the probes interact directly with the target nucleic acid (through first portions 16 and 22).

V.7 Libraries (Arrays) of Probes

Figure 5:
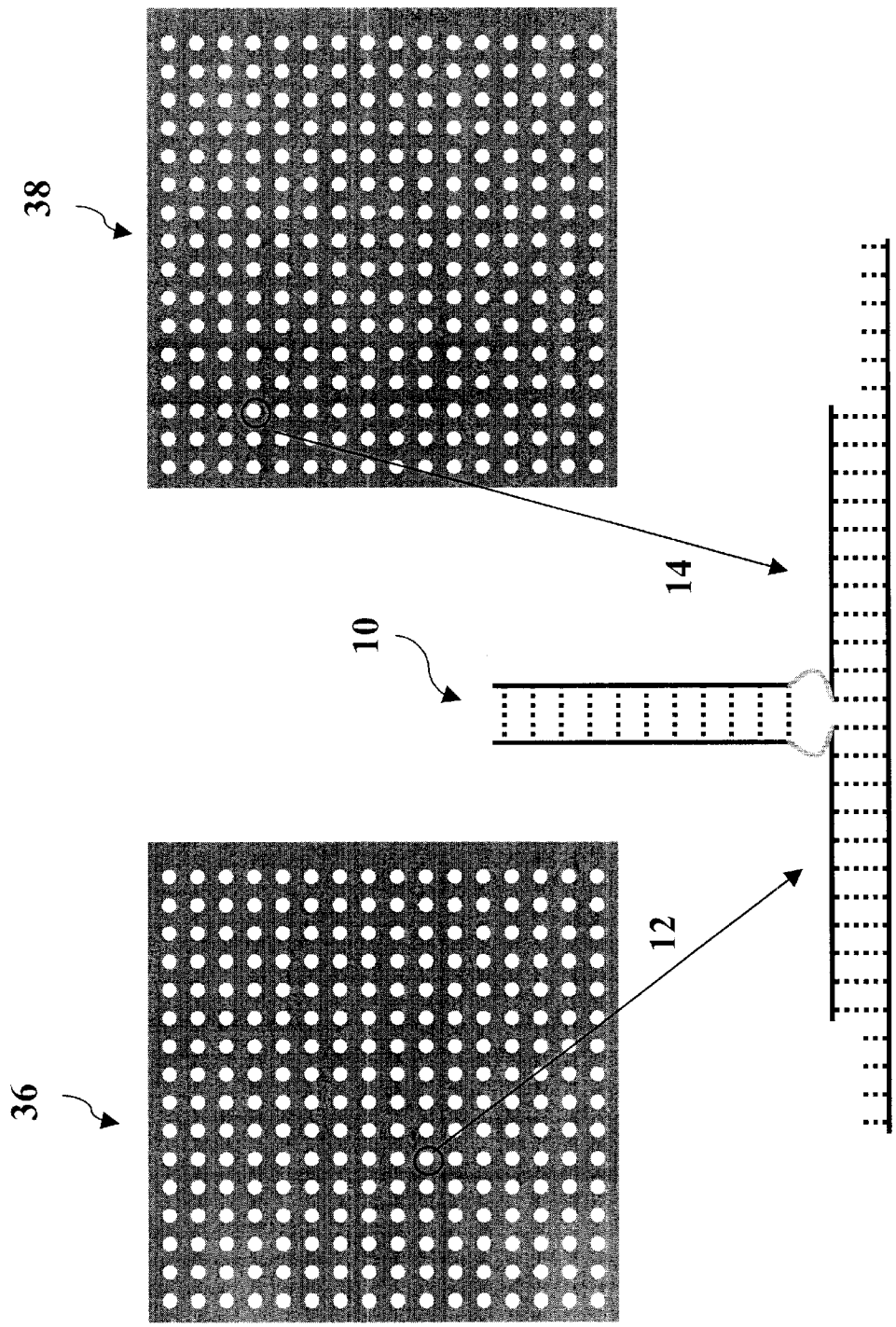
FIG. 5 schematically depicts an embodiment of a method of generating a binding moiety by selecting probes from libraries of the present invention.

In another embodiment, the invention relates to libraries of probes used to generate the above-described binding moieties. In this embodiment, the first portions of each of the first probes are complementary to a different sequence, and the first portions of each of the second probes are complementary to a different sequence. In a preferred embodiment, each of the second portions of each of the first probes is capable of hybridizing with any of the second portions of each of the second probes. Thus, as shown in FIG. 5, the skilled artisan can select one of the first probes 12 from a first array 36 of a plurality of first probes and one of the second probes 14 from a second array 38 of a plurality of second probes to generate a particular binding moiety 10.

Figure 6:
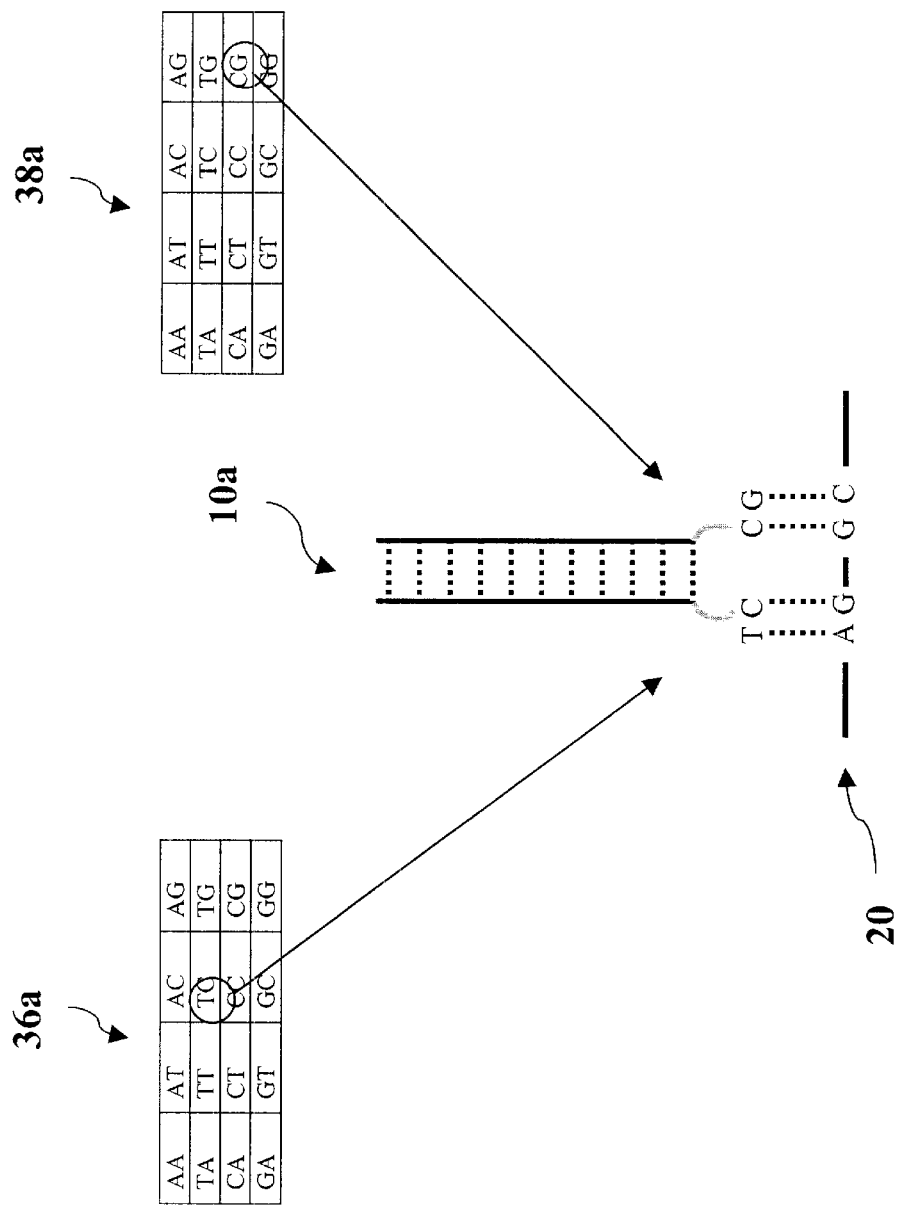
FIG. 6 schematically illustrates the conceptual structure of the libraries of the present invention by an exemplary depiction of dinucleotide regions of probes in libraries and formation of an adjacent three-way junction with a target sequence complementary to the two selected dinucleotide-containing probes.

Through judicious selection of a first probe and a second probe, the skilled artisan can generate a particular binding moiety complementary to a particular nucleotide sequence of interest. The theory underlying the selection process is depicted in FIG. 6. In FIG. 6, the skilled artisan is provided with a first array 36a of first probes. For simplicity in disclosing the general concept, and merely as exemplary, the first probes in FIG. 6 are each complementary to a dinucleotide sequence. It should be noted that in the actual practice of the invention, however, each of the first probes would be complementary to a sequence typically of from three to eight nucleotides in length. The complete array of dinucleotide sequences includes sixteen probes, each of which is complementary to a different nucleotide sequence. The position of each first probe in FIG. 6 is marked with the sequence of its first portion, although it should be realized that each of the first probes also has an identical second portion complementary to a second portion of the second probes in their respective array 38a. Similarly, the skilled artisan is provided with a second array 38a of second probes, each of which is complementary to a different dinucleotide sequence. The position of each second probe 14 is marked with the sequence of its first portion 22.

Continuing to refer to FIG. 6, to generate a binding moiety complementary to the sequence "CGGA", the skilled artisan selects probes for a binding moiety with nucleobases "TCCG". The skilled artisan selects from the first array 36a a first probe containing "TC" and selects from the second array 38a a second probe containing "CG" to form binding moiety 10a which together with target may form a three-way junction. Alternatively, if the skilled artisan wishes to generate a binding moiety containing "AAGT", the complement of the sequence "ACTT", the artisan would select a first probe containing "AA" and a second probe containing "GT". Thus, from two arrays of sixteen probes each, the artisan is provided with 256 possible binding moieties, one of which is 10a.

Accordingly, practice of the invention permits the skilled practitioner to use two or more low-complexity libraries to generate a probe, whereas a single high-complexity library would otherwise be necessary. For example, to generate a probe complementary to any twelve nucleotide region of a target nucleic acid without practicing this invention, one skilled in the art would require a library of $4^{12}$ or 16,777,216 probes. In contrast, when practicing this invention, the skilled practitioner instead could use a pair of libraries recognizing six nucleotides each, such that each library contained only $4^6$=4096 probes. Accordingly, in this example, the practice of this invention requires the presence of only 2×4096=8192 probes, which is less than 0.05% (8192÷16,777,216) of the number of probes that would otherwise be required. Alternatively, when practicing the invention the skilled practitioner could use three libraries recognizing four nucleotides each, such that each library contained only $4^4$=256 probes. The skilled artisan practicing the invention would thus require only 3×256=768 probes, less than 0.005% (768÷16,777,216) of the number of probes required without practicing the invention. Accordingly, the arrays of the present invention dramatically reduce the cost associated with producing, storing, and maintaining appropriate probe libraries.

An array of a plurality of probes preferably includes at least one probe capable of hybridizing to each possible first region of interest. For example, in FIG. 6, each first probe in the first array 36a was capable of hybridizing to one particular dinucleotide sequence. The first array included $4^2$ or 16 first probes, such that for any particular first region of interest, a probe was available to hybridize to it. In general, if each probe is complementary only to one particular nucleotide sequence of length x, the array should preferably include $4^x$ probes. Alternatively, a probe may be complementary to more than one particular nucleotide sequence, perhaps through the inclusion of one or more "universal" nucleobases capable of hybridizing to any of a plurality of naturally-occurring nucleobases in a target nucleic acid. Thus, more generally, the array preferably includes $4^x \div N$ probes, where N is the number of nucleotide sequences to which each probe is complementary, i.e. the degeneracy of the probe.

Accordingly, in one embodiment, a first array includes at least $0.5 \times 4^x \div N$ probes, where x is the length, in nucleotides, of the first region and where N is the degeneracy of the first probes (the number of nucleotide sequences to which each first probe is complementary). Preferably, in addition, a second array includes at least $0.5 \times 4^y \div M$ probes, where y is the length, in nucleotides, of the second region and where M is the degeneracy of the second probes. More preferably, the first array includes at least $0.5 \times 4^x \div N$ first probes and the second array includes at least $0.5 \times 4^Y \div M$ second probes. More preferably, x+y is from 6 to 12.

The skilled artisan will appreciate that the arrays of the present invention lend themselves to embodiments in which the selection of probes is partially or fully automated. Thus, for example, either the target nucleic acid sequence or its complement could be provided to a computer running a suitable software program. The software could then analyze the sequence and recommend one or more combinations of probes suitable for generating useful binding moieties. A software program could also retrieve the desired probes robotically, and may mix the probes in an appropriate combination. The software program for selecting the probes could be the same as the software program for manipulating the probes, or the programs could be partially or completely independent from each other. The software could incorporate other optional features as well, such as the ability to accept and store shipping or billing information, the ability to label the probes for shipping to an end user, or the ability to be accessed over the internet. Methods of building computerized systems capable of performing defined operations are well known in the art and need not be elaborated herein. Thus, in some embodiments, the selection and preparation of probes is fully automated. In other embodiments, the selection and preparation are done by humans with or without assistance from computerized systems.

V.8 Use of the Probes in Hybridizing to a Target Nucleic Acid

The binding moieties of the present invention are formed by combining at least a first probe and a second probe in solution. It is understood that one of the probes may optionally be immobilized on a solid support through an ionic interaction, affinity/receptor interaction, or covalent linkage (U.S. Pat. No. 5,639,609). The solid substrate may be particles, beads, membranes, frits, slides, plates, micromachined chips, alkanethiol-gold layers, non-porous surfaces, or other polynucleotide-immobilizing media. The solid substrate material may be polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of such. In another embodiment, the target nucleic acid may optionally be immobilized on a solid substrate of the same configurations and materials (U.S. Pat. No. 5,821,060).

The binding moieties can be used as other nucleic acids or nucleic acid analogs are used in the art. Thus, for example, the binding moieties can be used to hybridize to a ribonucleic acid (RNA) to modulate the expression and/or stability of the RNA. Modulation of RNA levels or expression can be useful in medical science, agricultural science, and in a wide variety of biotechnological processes.

The binding moieties can also be used to detect a nucleotide sequence of a nucleic acid or a nucleic acid analog. Detection could be accomplished, for example, during gel electrophoresis of nucleic acids or nucleic acid analogs by providing a detectable binding moiety within the gel. Detection could be accomplished following gel electrophoresis and transfer to a blot (e.g. nitrocellulose or nylon) by contacting the blot with a solution including a detectable binding moiety. Detection could be accomplished in situ in a cell or a tissue by contacting the cell or tissue with a solution including a detectable binding moiety. Detection could be accomplished in solution by observing changes in the physico-chemical properties of the target nucleic acid or nucleic acid analog after exposure to a binding moiety. In a preferred embodiment, detection of the binding event is facilitated by the presence of a detectable moiety, such as a fluorescent moiety, on at least one of the probes.

Because the invention provides the skilled artisan a means to generate a wide variety of binding moieties quickly and efficiently, many binding moieties may be used to analyze a sequence of interest. Thus, for example, a variety of binding moieties complementary to a particular RNA can be screened for their effects on the translation of the RNA. Nucleic acids could be screened for the presence of polymorphisms (e.g. single nucleotide polymorphisms) or mutations. Once a particular sequence of interest has been identified, further analysis is possible using the binding moieties of the present invention or using the oligonucleotide probes of the prior art.

Exposure of the target nucleic acid to the binding moiety may optionally occur in the presence of a hybridization-stabilizing moiety such as a minor groove binder, an intercalator, a polycation such as poly-lysine or spermine, or a cross-linking functional group. Hybridization-stabilizing moieties may increase the stability of base-pairing (affinity), or the rate of hybridization, exemplified by high thermal melting temperatures ($T_m$) of the duplex. Hybridization stabilizing moieties serve to increase the specificity of base-pairing, exemplified by large differences in $T_m$ between perfectly complementary oligonucleotide and target sequences and where the resulting duplex contains one or more mismatches of Watson/Crick or Hoogsteen-type base-pairing ("DNA and RNA structure" in *Nucleic Acids in Chemistry and Biology*, (1996) G. Blackburn and M. Gait, eds., $2^{nd}$ edition, Oxford University Press, pp. 15–81). A preferred minor groove binder is $CDPI_3$ (E. Lukhtanov etal., WO 96/32496; Lukhtanov etal (1995) Bioconjugate Chem. 6:418–26).

V.9 Use of Multipartite Binding Moieties in Priming Enzyme-Catalyzed Reactions The binding moieties can also be used as primers for enzyme-catalyzed reactions such as primer extension. When used as primers, the binding moieties should include at least a portion of a nucleic acid at the terminus of one of the probes. When the nucleic acid is present and hybridized to a complementary nucleic acid or nucleic acid analog, an appropriate enzyme (e.g. DNA-dependent DNA polymerase, RNA-dependent DNA polymerase, DNA-dependent RNA polymerase, and the like) can catalyze a reaction for which the binding moiety serves as a primer.

Primer extension is initiated at the template site where a primer anneals. One or more different nucleotide 5'-triphosphates may be present in the reaction mixture such that the complementary nucleotide is incorporated by a polymerase enzyme according to the template sequence. Extension of the primer continues until nucleotides are depleted, the enzyme is no longer functional, or termination occurs by incorporation of a terminating nucleotide that will not support continued DNA elongation. Chain-terminating nucleotides are typically 2',3'-dideoxynucleotide 5'-triphosphates (ddNTP) that lack the 3'-OH group necessary for 3' to 5' DNA chain elongation. Other terminating nucleotides include 2',3'-dideoxydehydro-; 2'-acetyl; 2'-deoxy, halo; and other 2'-substituted nucleotide 5'-triphosphates.

In general, the reaction conditions for primer extension involve an appropriate buffering system to maintain a constant pH. Also present are a divalent cation, a binding moiety of the present invention, a target nucleic acid, nucleotide 5'-triphosphates, and a polymerase. Additional primer extension reagents, such as reducing agents, monovalent cations, or detergents may be added to enhance the reaction rate, fidelity, or other parameters. Different polymerases may have different optimal pH values or ion concentrations. In some embodiments, a preferred polymerase is thermostable. Kits useful in the practice of the invention may combine any or all of the above reagents.

Nucleotide 5'-triphosphates may be labelled for use in methods of the invention. The sugar or nucleobase moieties of the nucleotides may be labelled. Preferred nucleobase labelling sites include the 8-C of a purine nucleobase, the 7-C or 8-C of a 7-deazapurine nucleobase, and the 5-position of a pyrimidine nucleobase. The labelled nucleotide is enzymatically incorporatable and enzymatically extendable. Labelled nucleotide 5'-triphosphates may have the following formula:

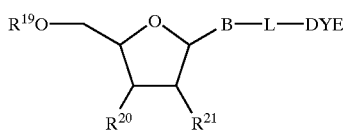

where DYE is a protected or unprotected dye, including energy transfer dye. B is a nucleobase, e.g. uracil, thymine, cytosine, adenine, 7-deazaadenine, guanine, and 8-deazaguanosine. $R^{19}$ is triphosphate, thiophosphate, or phosphate ester analog. $R^{20}$ and $R^{21}$, when taken alone, are each independently H, HO, and F. Linker L may be:

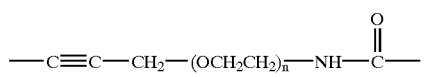

wherein n is 0, 1, or 2.

Labeled primer extension products, "fragments," are generated through template-directed enzymatic synthesis using labeled binding moieties or nucleotides. The fragments can be separated by a size-dependent process, e.g., electrophoresis or chromatography, and the separated fragments detected, e.g., by laser-induced fluorescence. In a preferred fragment analysis method, i.e., Sanger-type sequencing, a binding moiety is extended by a DNA polymerase in vitro using a single-stranded or double-stranded DNA template whose sequence is to be determined. Extension is initiated at a defined site based on where a binding moiety anneals to the template. The extension reaction is terminated by incorporation of a nucleotide that will not support continued DNA elongation, i.e., a terminating nucleotide. When optimized concentrations of dNTP and terminating nucleotides are used, enzyme-catalyzed polymerization (extension) will be terminated in a fraction of the population of chains at each site where the terminating nucleotide is incorporated such that a nested set of primer extension fragments result. If fluorescent dye-labeled binding moieties or labeled terminating nucleotides are used for each reaction, the sequence information can be detected by fluorescence after separation by high-resolution electrophoresis (U.S. Pat. No. 5,821,058). Each of the four possible terminating nucleotides (A, G, C, T) may be present in the extension reaction and bear a different spectrally-resolvable fluorescent dye (U.S. Pat. No. 5,366,860).

The binding moieties of the present invention may also be used in "mini-sequencing," another application involving incorporation of terminating nucleotides to determine the identity, presence, or absence of a nucleotide base at a specific position in a target nucleic acid (U.S. Pat. No. 5,888,819; A. Syvanen et al., (1990) "A primer-guided nucleotide incorporation assay in the genotyping of apolipoprotein E," Genomics 8:684–92). Genotype determination based on identification of different alleles is based on single nucleotide polymorphisms (SNPs). SNPs can be detected by ddNTP incorporation from binding moieties annealed immediately adjacent to the 3' end of the SNP site of the target nucleic acid sequence to be determined, and detection of the extension products by MALDI-TOF mass spectroscopy. The mass difference resulting from incorporation of different dideoxynucleotides can be accurately determined by mass spectrometry. More than one binding moiety, with different sequences and masses, can be used in the same reaction to simultaneously detect multiple SNPs by analyzing the mass spectra of the extension products (U.S. Pat. No. 5,885,775).

Primed in situ labeling (PRINS) is a molecular cytogenetic technique that combines the high sensitivity of PCR with the cellular or chromosomal localization of fluorescent signals provided by in situ hybridization. PRINS can be conducted by annealing unlabeled binding moieties to complementary target nucleic acids, followed by a DNA polymerase extension in the presence of labeled dNTP. Preferably the labels are fluorescent dyes, so that the extension products can be detected and/or measured by fluorescence detection (J. Koch et a., (1991) Genet. Anal. Tech. Appl. 8:171–78).

The invention is illustrated further by the following non-limiting examples.

VI. EXAMPLES

Example 1.

Synthesis of Probes

PNA probes may be synthesized at any scale from commercially available reagents and automated synthesizers, following the manufacturers' protocols. Most conveniently, PNA is synthesized at the 2 µmole scale, using Fmoc/Bhoc, tBoc/Z, or MMT protecting group monomers on an Expedite Synthesizer (PE Biosystems) on XAL or PAL support, on the Model 433A Synthesizer (PE Biosystems) on MBHA support, or on other automated synthesizers. After synthesis is complete, the crude PNA is cleaved from the support, e.g. with trifluoroacetic acid, and then precipitated with diethylether and washed twice in diethylether. PNA may be purified by reverse-phase HPLC, analyzed by mass spectroscopy, and quantitated by correlating absorbance at 260 nm with mass.

Oligonucleotide probes may be synthesized from commercially available (PE Biosystems) nucleoside phosphoramidites (U.S. Pat. No. 4,415,732) and solid supports, e.g. silica, controlled-pore-glass (U.S. Pat. No. 4,458,066) and polystyrene (U.S. Pat. Nos. 5,047,524 and 5,262,530). The phosphoramidite chemistry method of oligonucleotide synthesis is routinely automated on commercially available synthesizers (Model 394 DNA/RNA Synthesizer, PE Biosystems).

Labelling probes

Labelling typically results from mixing an appropriate reactive label and a probe in a suitable solvent in which both are soluble, using methods well-known in the art (Hermanson, *Bioconjugate Techniques*, (1996) Academic Press, San Diego, Calif. pp. 40–55, 643–71), followed by separation of the labelled probe from any starting materials or unwanted by-products. The labelled oligonucleotide can be stored dry or in solution for later use, preferably at low temperature.

The label may include a reactive linking group at one of the substituent positions, e.g. 5- or 6-carboxy of fluorescein or rhodamine, for covalent attachment to a probe. Reactive linking groups are moieties capable of forming a covalent bond, typically electrophilic functional groups capable of reacting with nucleophilic groups on a probe, such as amines and thiols. Examples of reactive linking groups include succinimidyl ester, isothiocyanate, sulfonyl chloride, sulfonate ester, silyl halide, 2,6-dichlorotriazinyl, pentafluorophenyl ester, phosphoramidite, maleimide, haloacetyl, epoxide, alkylhalide, allyl halide, aldehyde, ketone, acylazide, anhydride, and iodoacetamide.

A preferred reactive linking group of a fluorescent dye is an N-hydroxysuccinimidyl ester (NHS) of a carboxyl group substituent of the fluorescent dye. The NHS ester of the dye may be preformed, isolated, purified, and/or characterized, or it may be formed in situ and reacted with a nucleophilic group of an oligonucleotide. Typically, a carboxyl form of the dye is activated by reacting with some combination of a carbodiimide reagent, e.g. dicyclohexylcarbodiimide, diisopropylcarbodiimide, or a uronium reagent, e.g. TSTU (O-(N-Succinimidyl) -N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the dye.

The linker between a probe and a label may be: (i) a covalent bond; (ii) an alkyldiyl —$(CH_2)_n$—, where n is 1 to 12; (iii) ethyleneoxy —$(CH_2CH_2O)n$—, where n is 1 to 12, (iv) aryldiyl ($C_6$ to $C_{20}$); or (v) one or more amino acids. Lysine, aspartic acid, and glutamic acids are preferred amino acid linkers in PNA probes. The sidechain, $\epsilon$-amino group of lysine may be the reactive linking group for attachment of a label, e.g. reporter dye or quencher. Linkers are typically attached to the amino and/or carboxyl terminus of the PNA by the corresponding monomer units with compatible protecting groups and reactive functionality for condensation with PNA monomer units and the solid support. For example, the O linker (2-[2-(2-aminoethoxy]acetic acid can be attached to the amino terminus of any PNA backbone amino group, or on amino functionality of a solid support. The 5' hydroxyl terminus or a nucleobase are preferred attachment sites on oligonucleotide probes.

PNA probe ME01 (CAGTCAGT-O-CCCAGCCTAT-Lys-Flu; wherein O denotes the O linker, Lys denotes lysine and Flu refers to carboxyfluorescein and PNA probe ME02 (Rho-O-ATAGCCCAGC-O-ACTGACTG; wherein Rho represents tetramethylrhodamine) were synthesized on Expedite Nucleic Acid Synthesis System 8909 (PE Biosystems) employing commercially available Fmoc (Bhoc) monomers (PE Biosystems). The synthesis, labeling, purification and analysis were performed according to the manufacturer's instructions as described in "PNA synthesis for the Expedite Nucleic Acid Synthesis System" (part number 601308), the teachings of which are herein incorporated by reference.

Example 2.

Detection of a Target Nucleic Acid

PNA can hybridize to its target complement in either a parallel or anti-parallel orientation. However, the anti-parallel duplex (where the carboxyl terminus of PNA is aligned with the 5' terminus of DNA, and the amino terminus of PNA is aligned with the 3' terminus of DNA) is typically more stable (Egholm, etal (1993) "PNA hybridizes to complementary oligonucleotides obeying the Watson-Crick hydrogen bonding rules", Nature 365:566–68). The PNA FRET probes of the present invention are designed such that the PNA anneals in the anti-parallel orientation with the target sequences.

Figure 7:
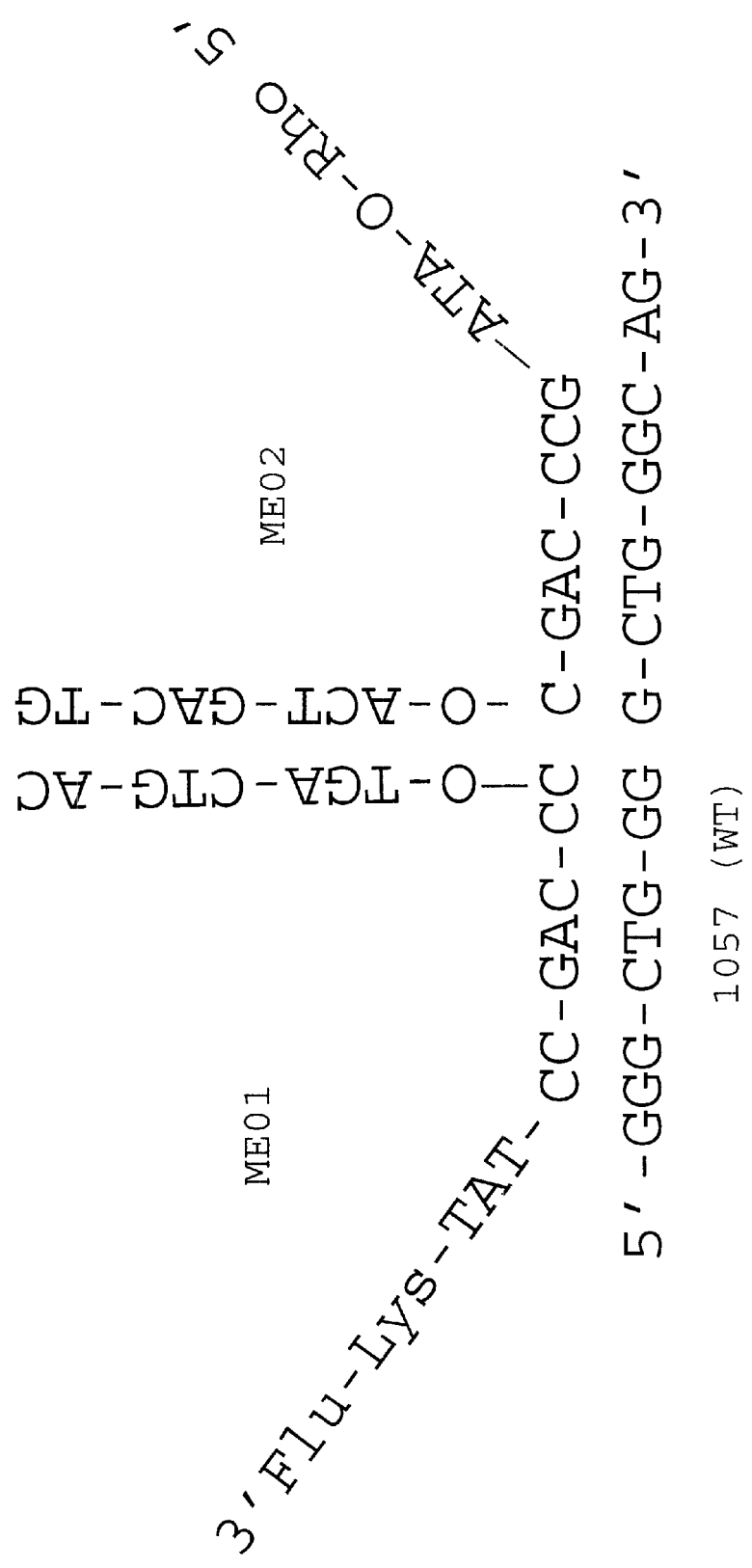
FIG. 7 shows a three-way junction formed from fluorescein-labelled (Flu) ME01 PNA, rhodamine-labelled (Rho) ME02 PNA, and 1057 wild-type DNA.

PNA molecules ME01 and ME02 were combined with DNA molecule 1057 as a model target:

GGGCTGGGGCTGGGCAG (SEQ ID NO:1)

in 50 μL of 100 mM Tris-HCl, pH 8 to form the three-way junction shown in FIG. 7. The final concentration of each PNA and DNA molecule was 1 μM. The mixtures were incubated at 95° C. for 10 minutes and gradually cooled to 37° C. over one hour in a PE GeneAmp PCR System 9700 thermocycler (PE Biosystems). Five picomoles of the product were mixed with a Hi-Density TBE (Tris (hydroxymethyl)aminomethane (Tris)-buffered ethylenediaminetetraacetic acid (EDTA)) sample buffer. The resulting solution contained 45 mM Tris base, 45 mM boric acid, 0.4 mM EDTA, 3% (v/v) Ficoll, 0.02% bromophenol blue, and 0.02% xylene cyanol.

This solution, and others detailed below, was electrophoresed under both native (non-denaturing) and denaturing conditions. Native PAGE (FIG. 8) was conducted at room temperature and without urea in the gel formulation. Denaturing PAGE (FIG. 9) was conducted on a 10% denaturing PAGE gel ("15% TBE-urea gel", Novex, San Diego, Calif.) at 35° C. and about 130V for about 40 minutes. Both conditions included 10% polyacrylamide, run in 1xTBE (89 mM Tris base, 89 mM boric acid, 2 mM EDTA, pH 8.3. Samples were loaded onto the gels, electrophoresed, and visualized by fluorescence detection under short wavelength UV light.

The presence of the annealed complex could be detected in lane 1 under both native (FIG. 8) and denaturing (FIG. 9) conditions by fluorescence of the carboxyfluorescein (Flu) and TAMRA (Rho) labels. The neutral PNA probes, ME01 or ME02, do not migrate from the well during electrophoresis. The PNA-PNA-DNA complex (FIG. 7) was stable even under the stringent denaturing conditions (FIG. 9). The complex required the presence of both PNA molecules. If either was omitted, no complex formation was observed.

Example 3.

Specificity of the Complex

PNA molecules ME01 and ME02 were combined either with the complementary DNA molecule 1057, as above, or with DNA molecule 1058:

GGGCTGCCCTTTCTGGGCAG (SEQ ID NO. 2)

which bears a three nucleotide insertion (mut3bp) when compared to 1057, or with DNA molecule 1059:

GGGCTCGGGCTGGGCAG (SEQ ID NO. 3)

which bears a single nucleotide substitution (mut1bp). Annealing, electrophoresis and detection were carried out as described in Example 2. Under native conditions, three-way junction complexes were formed for each DNA (FIG. 8, lanes 1–3). Under denaturing conditions (FIG. 9), although the PNA-PNA-DNA complex was clearly evident when the complementary target sequence of 1057 was present (lane 1), no stable complex formation was observed in the presence of the mismatch of 1059 (lane 2) or in the presence of the three nucleotide insertion of 1058 (lane 3). The specificity of two PNA probes each with 7 base first portions hybridizing to target and 8 base second portions hybridizing to each other is thus demonstrated.

Example 4.

Importance of the Second Portion of the Probe

PNA molecule ME01 was combined with DNA molecule 1057 in the presence of either PNA molecule ME02 or ME03 (Rho-O-ATAGCCCAGC-O), which lacks the second portion used by ME02 for interaction with ME01. Annealing was performed as described in Example 2. The annealing product was mixed with sample buffer to a final concentration of 45 mM Tris base, 45 mM boric acid, 0.4 mM EDTA, 0.15g/mL Ficoll, and 0.07% xylene cyanol. The sample was electrophoresed under the same native (FIG. 8, lane 4) and denaturing (FIG. 9, lane 4) conditions as described in Example 2. The single PNA probe ME02 with a 7 base first portion hybridizing to target 1057 gave no observable duplex formation even under native conditions.

Although some ME01/ME03/1057 complex formation was observed (result not shown), complex formation was significantly reduced when compared to the ME01/ME02/1057 complexes, despite the relatively permissive conditions of the gel.

A single PNA probe 1133 (Rho-O-GCCCAGC-O-CCCAGCC) with 14 bases hybridizing to target was hybridized with each of the three targets; 1057 (lane 5), 1059 (lane 6), and 1058 (lane 7) under native and denaturing conditions. The PNA nucleobases in 1133 bind to target 1057 with an O linker bulge in 1133, and additionally the C/G mismatch with 1059. The duplex between 1133 and 1058 has the O linker bulge in 1133 and a three base TTT bulge in 1058. Under native conditions, stable duplexes were observed with each of the three targets, but under the more stringent denaturing conditions, only the O linker bulge duplex in lane 5 formed a stable duplex.

A single PNA probe 1134 (Rho-O-GCCCAGCCCCAGCC) differs from 1133 only by the absence of the O linker in the middle of the sequence. PNA probe 1134 was also hybridized with each of the three targets; 1057 (lane 8), 1059 (lane 9), and 1058 (lane 10) under native and denaturing conditions. The PNA nucleobases in 1134 bind to target 1057 as a perfect match, and to 1059 with a single mismatch. The duplex between 1134 and 1058 has a three base TTT bulge in 1058. Under native conditions (FIG. 8), approximately equally stable duplexes were observed with each of the three targets. Under the more stringent denaturing conditions (FIG. 9), the perfect match (lane 8) showed the most intense band, although mismatch duplexes are observed in lanes 9 and 10. Therefore little specificity is observed in duplex formation with a single PNA probe with 14 bases hybridizing to target. Thus, the second portions of two probes, which mediate the direct interaction between the PNA molecules, is important both to the stability of the tripartite complex and specific detection of target nucleic acid.

PNA probes with shorter first portions binding to target were investigated (lanes 11, 12, 13). Unlabelled PNA probe 1136 (O-CAGTCAGT-O-CCCAG), rhodamine labelled PNA probe 1137 (Rho-O-CCAGC-O-ACTGACTG) were annealed under the conditions of Experiment 2 with perfect match target 1057 (lane 11), one base mismatch target 1059 (lane 12), and three base bulge 1058 (lane 13). Each sample was electrophoresed under native (FIG. 8) and denaturing conditions (FIG. 9). Probe 1136 has a five base first portion hybridizing to target and probe 1137 has a six base first portion hybridizing to target. Probe 1137 has the rhodamine dye attached directly to the 5' terminus of C base which binds to target and is without the non-binding sequence (ATA) present in probe ME02. Probes 1136 and 1137 hybridize to each other by an eight base second portion. No stable complexes are observed with the three samples under even the native electrophoresis conditions.

PNA probes ME01 and 1137 were investigated for complex formation by annealing with targets 1057 (lane 14), 1058 (lane 15), and 1059 (lane 16) under the conditions of Experiment 2. Samples were electrophoresed under native (FIG. 8) and denaturing conditions (FIG. 9). Specificity was observed under native conditions where only the perfect match complex was observed (FIG. 8, lane 14). No duplex was observed with PNA probe 1137 alone binding with perfect match target 1057 (lane 17).

PNA probes 1136 and ME02 were investigated for complex formation by annealing with targets 1057 (lane 18), 1058 (lane 19), and 1059 (lane 20) under the conditions of Experiment 2. Specificity was observed under native conditions where only the perfect match complex was observed (FIG. 8, lane 18).

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Each of the patent documents and scientific publications disclosed hereinabove is incorporated by reference herein.

What is claimed is:

1. A first array of a plurality of single-stranded first probes and a second array of a plurality of single-stranded second probes, wherein the first probes comprise a first portion complementary to a first region of a target nucleic acid and capable of hybridizing thereto, and a second portion capable of hybridizing with the second probe, wherein the first and second portions of the first probe are joined by a flexible linker, wherein the flexible linker comprises 1 to 6 ethyleneoxy units, alkyldiyl of 1 to 20 carbon atoms, or aryldiyl of 6 to 20 carbons atoms; and the second probes comprise a first portion complementary to a second region of the target nucleic acid and capable of hybridizing thereto, and a second portion capable of hybridizing with the first probe;

the first region of the target nucleic acid and the second region of the target nucleic acid are substantially adjacent;

each of the first and the second region of the target nucleic acid is from three to eight nucleotides in length;

at least one of the first probe or the second probe comprises a high-affinity nucleic acid analog;

at least one of the first probe or the second probe comprises a fluorescent detection moiety;

the portion of each of the first probes complementary to the first region of the target nucleic acid has a different sequence, wherein the first region of the target nucleic acid is x nucleotides in length and x is greater than or equal to 6;

the array of first probes comprises at least $(0.5 \times 4^x) \div N$ first probes, wherein N is equal to the degeneracy of each of the first portions of each of the first probes; and the portion of each of the second probes complementary to the second region of the target nucleic acid has a different sequence.

2. The first array and second array of claim 1 wherein the second region of the target nucleic acid is y nucleotides in length and y is greater than or equal to 6, and wherein the array of second probes comprises at least $(0.5 \times 4^y) \div M$ second probes, wherein M is equal to the degeneracy of each of the first portions of each of the second probes.

3. The first array and second array of claim 1 wherein the second portion of a said first probe and the second portion of a said second probe comprise regions which are complementary to each other; and wherein the first and second portions of the second probe are joined by a flexible linker, wherein the flexible linker comprises 1 to 6 ethyleneoxy units, alkyldiyl of 1 to 20 carbon atoms, or aryldiyl of 6 to 20 carbon atoms.

4. The first array and second array of claim 1 wherein the second portion of a said first probe hybridizes with a greater binding affinity with the second portion of a said second probe than with any portion of the target nucleic acid.

5. The first array and second array of claims 1 wherein the portion of a said first probe complementary to the first region of a target nucleic acid comprises a high-affinity nucleic acid analog.

6. The first array and second array of claim 1 wherein the high-affinity nucleic acid analog comprises one or more PNA monomer units.

7. The first array and second array of claim 6 wherein the peptide nucleic acid has a 2-aminoethylglycine backbone.

8. The first array and second array of claim 1 wherein a probe comprises a quenching moiety.

9. The first array and second array of claim 1 wherein a probe comprises an oligonucleotide sequence.

10. The first array and second array of claim 1 wherein a said second probe further comprises a flexible linker selected from 1 to 6 ethyleneoxy units, alkyldiyl of 1 to 20 carbon atoms, and aryldiyl of 6 to 20 carbon atoms.

11. The first array and second array of claim 1 wherein a probe is immobilized on a solid support.

12. The first array and second array of claim 1 wherein the target nucleic acid is immobilized on a solid support.

13. The first array and second array of claim 1 wherein the high-affinity nucleic acid analog are selected from locked nucleic acids, 2'-O-methyl nucleic acids, and 2'-fluoro nucleic acids.

14. The first array and second array of claim 1 wherein the second portion of a said first probe and the second portion of a said second probe comprise an isocytosine-isoguanine base pair.

15. A kit comprising the first array of a plurality of first probes of claim 1 and a buffer.

16. The kit of claim 15 further comprising the second array of a plurality of second probes.

17. The kit of claim 15 further comprising an enzyme.

* * * * *